| (12) | United States Patent | (10) Patent No.: | US 8,796,038 B2 |
|---|---|---|---|
| | Williamson, IV et al. | (45) Date of Patent: | Aug. 5, 2014 |

(54) METHOD FOR ORIENTING TISSUE SAMPLES ON A MICROTOME SECTIONABLE BIOPSY SUPPORT

(71) Applicants: Biopath Automation, L.L.C., Loveland, OH (US); Sakura Finetek U.S.A., Inc., Torrance, CA (US)

(72) Inventors: Warren P. Williamson, IV, Loveland, OH (US); Stephen P. Whitlatch, Cincinnati, OH (US); Carlos A. Saez, Irvine, CA (US)

(73) Assignees: Biopath Automation, L.L.C., Loveland, OH (US); Sakura Finetek U.S.A., Inc., Torrance, CA (US)

( * ) Notice: Subject to any disclaimer, the term of this patent is extended or adjusted under 35 U.S.C. 154(b) by 0 days.

(21) Appl. No.: 13/678,846

(22) Filed: Nov. 16, 2012

(65) Prior Publication Data

US 2013/0078670 A1 Mar. 28, 2013

Related U.S. Application Data

(62) Division of application No. 12/692,208, filed on Jan. 22, 2010, now Pat. No. 8,329,120.

(60) Provisional application No. 61/146,444, filed on Jan. 22, 2009, provisional application No. 61/238,913, filed on Jan. 1, 2009.

(51) Int. Cl.
| G01N 1/06 | (2006.01) |
|---|---|
| G01N 1/31 | (2006.01) |
| G01N 1/36 | (2006.01) |
| G01N 33/483 | (2006.01) |

(52) U.S. Cl.
CPC *G01N 1/06* (2013.01); *G01N 1/312* (2013.01); *G01N 1/36* (2013.01); *G01N 33/4833* (2013.01)

USPC .......................................... 436/172; 422/500

(58) Field of Classification Search
CPC ........... G01N 1/06; G01N 1/312; G01N 1/36; G01N 33/4833
USPC .......................................... 436/172; 422/500
See application file for complete search history.

(56) References Cited

U.S. PATENT DOCUMENTS

| 1,885,138 A | 11/1932 | Pilson |
|---|---|---|
| 2,749,909 A | 6/1956 | Ullery |

(Continued)

FOREIGN PATENT DOCUMENTS

| CN | 1684772 A | 10/2005 |
|---|---|---|
| EP | 0139424 A2 | 5/1985 |

(Continued)

OTHER PUBLICATIONS

U.S. Patent and Trademark Office, International Search Report and Written Opinion in corresponding PCT Serial No. PCT/US04/33604, Nov. 15, 2005, 13 pgs.

(Continued)

*Primary Examiner* — Sam P Siefke

(74) *Attorney, Agent, or Firm* — Wood, Herron & Evans, L.L.P.

(57) ABSTRACT

Tissue orientation devices include a perforated tissue support with at least one perforated channel for receiving a tissue sample, and a plurality of tabs configured to extend along and into the channel to retain the tissue sample during processing and embedding. Tissue orientation devices include elongated legs coupled together for holding one or more biopsy tissue samples therebetween. Associated methods include using the cassettes and orientation devices to hold and orient tissue samples for processing, embedding and microtome sectioning.

7 Claims, 17 Drawing Sheets

(56) References Cited

U.S. PATENT DOCUMENTS

| | | |
|---|---|---|
| 2,776,596 A | 1/1957 | Eigen |
| 2,996,762 A | 8/1961 | McCormick |
| 3,224,434 A | 12/1965 | Molomut et al. |
| 3,257,279 A | 6/1966 | Schain |
| 3,527,863 A | 9/1970 | Weichselbaum |
| 3,587,872 A | 6/1971 | Pauly |
| 3,624,197 A | 11/1971 | Schain |
| 3,679,450 A | 7/1972 | Beightol |
| 3,691,097 A | 9/1972 | Stiles et al. |
| 3,723,061 A | 3/1973 | Stahl |
| 3,777,882 A | 12/1973 | McIntyre |
| 3,814,670 A | 6/1974 | Freake et al. |
| 3,874,851 A | 4/1975 | Wilkins et al. |
| 3,961,097 A | 6/1976 | Gravlee, Jr. |
| 3,982,862 A | 9/1976 | Pickett et al. |
| 3,996,326 A | 12/1976 | Schachet |
| 4,025,306 A | 5/1977 | Studer |
| 4,199,558 A | 4/1980 | Henderson |
| 4,219,334 A | 8/1980 | Schluter et al. |
| 4,220,252 A | 9/1980 | Beall et al. |
| 4,224,277 A | 9/1980 | Macho et al. |
| 4,261,474 A | 4/1981 | Cohen |
| 4,340,066 A | 7/1982 | Shah |
| 4,353,856 A | 10/1982 | Muck et al. |
| 4,427,614 A | 1/1984 | Barham et al. |
| 4,435,507 A | 3/1984 | Stenkvist |
| 4,439,319 A | 3/1984 | Rock |
| 4,446,900 A | 5/1984 | Markovich |
| 4,497,792 A | 2/1985 | Gindler |
| 4,545,831 A | 10/1985 | Ornstein |
| 4,557,903 A | 12/1985 | McCormick |
| 4,569,647 A | 2/1986 | McCormick |
| 4,576,796 A | 3/1986 | McCormick |
| 4,627,129 A | 12/1986 | Wittes |
| 4,656,047 A | 4/1987 | Kok et al. |
| 4,695,339 A | 9/1987 | Rada |
| 4,733,806 A | 3/1988 | Sloop |
| 4,752,347 A | 6/1988 | Rada |
| 4,801,553 A | 1/1989 | Owen et al. |
| 4,817,631 A | 4/1989 | Schnepp-Pesch et al. |
| 4,820,504 A | 4/1989 | Battifora |
| 4,834,943 A | 5/1989 | Yoshiyama |
| 4,839,194 A | 6/1989 | Malluche et al. |
| 4,849,173 A | 7/1989 | Chang |
| 4,870,975 A | 10/1989 | Cronk et al. |
| 4,887,612 A | 12/1989 | Esser et al. |
| 4,893,982 A | 1/1990 | Yamaguchi |
| 4,961,432 A | 10/1990 | Guirguis |
| 4,962,036 A | 10/1990 | Cermak et al. |
| 4,971,783 A | 11/1990 | Bolton et al. |
| 4,971,912 A | 11/1990 | Buhl et al. |
| 4,984,355 A | 1/1991 | Lubrano et al. |
| 4,985,206 A | 1/1991 | Bowman et al. |
| 4,997,100 A | 3/1991 | Dudek |
| 5,002,184 A | 3/1991 | Lloyd |
| 5,009,088 A | 4/1991 | Cislo |
| 5,024,830 A | 6/1991 | Linner |
| 5,047,008 A | 9/1991 | de Juan, Jr. et al. |
| 5,057,546 A | 10/1991 | Sudan |
| 5,077,012 A | 12/1991 | Guirguis |
| 5,080,869 A | 1/1992 | McCormick |
| 5,115,816 A | 5/1992 | Lee |
| 5,127,537 A | 7/1992 | Graham |
| 5,132,758 A | 7/1992 | Minami et al. |
| 5,137,710 A | 8/1992 | Smalley et al. |
| 5,143,714 A | 9/1992 | Cosgrove et al. |
| D330,257 S | 10/1992 | Schneider |
| 5,170,800 A | 12/1992 | Smith et al. |
| 5,172,700 A | 12/1992 | Bencini et al. |
| 5,217,479 A | 6/1993 | Shuler |
| 5,224,488 A | 7/1993 | Neuffer |
| 5,272,093 A | 12/1993 | Silva et al. |
| 5,279,800 A | 1/1994 | Berry, Jr. |
| 5,284,753 A | 2/1994 | Goodwin, Jr. |
| 5,308,758 A | 5/1994 | Dahl |
| 5,312,758 A | 5/1994 | Ahlqvist |
| 5,318,589 A | 6/1994 | Lichtman |
| 5,340,551 A | 8/1994 | Berry, Jr. |
| 5,350,150 A | 9/1994 | Fiore |
| 5,354,370 A | 10/1994 | Schmehl |
| 5,360,828 A | 11/1994 | Morrison |
| 5,411,885 A | 5/1995 | Marx |
| 5,427,742 A | 6/1995 | Holland |
| 5,533,642 A | 7/1996 | Lafond et al. |
| 5,586,438 A | 12/1996 | Fahy |
| 5,609,827 A | 3/1997 | Russell et al. |
| 5,650,327 A | 7/1997 | Copeland et al. |
| 5,665,398 A | 9/1997 | McCormick |
| 5,683,786 A | 11/1997 | Kavanaugh |
| 5,702,185 A | 12/1997 | Heikal |
| 5,718,916 A | 2/1998 | Scherr |
| 5,817,032 A | 10/1998 | Williamson, IV et al. |
| 5,867,102 A | 2/1999 | Souder et al. |
| 5,919,553 A | 7/1999 | Kavanaugh |
| 5,928,934 A | 7/1999 | McCormick |
| 5,963,368 A | 10/1999 | Domanik et al. |
| 5,968,436 A | 10/1999 | Takezaki |
| 6,017,476 A | 1/2000 | Renshaw |
| 6,148,878 A | 11/2000 | Ganz et al. |
| 6,193,102 B1 | 2/2001 | Bevirt et al. |
| 6,207,408 B1 | 3/2001 | Essenfeld et al. |
| D448,487 S | 9/2001 | Saez et al. |
| 6,289,682 B1 | 9/2001 | Rada |
| 6,387,653 B1 | 5/2002 | Voneiff et al. |
| 6,395,234 B1 | 5/2002 | Hunnell et al. |
| 6,395,373 B2 | 5/2002 | Conti et al. |
| 6,411,434 B1 | 6/2002 | Eastman et al. |
| 6,486,783 B1 | 11/2002 | Hausladen et al. |
| 6,489,171 B1 | 12/2002 | Aghassi et al. |
| 6,495,104 B1 | 12/2002 | Unno et al. |
| 6,498,032 B1 | 12/2002 | Clements et al. |
| 6,513,673 B2 | 2/2003 | Alley |
| 6,520,544 B1 | 2/2003 | Mitchell et al. |
| 6,560,837 B1 | 5/2003 | Hodjat et al. |
| 6,797,928 B2 | 9/2004 | Giberson et al. |
| 7,005,110 B2 | 2/2006 | Taft et al. |
| 7,156,814 B1 | 1/2007 | Williamson, IV et al. |
| 7,179,424 B2 | 2/2007 | Williamson, IV et al. |
| 7,780,919 B2 | 8/2010 | McCormick |
| 2001/0000487 A1 | 4/2001 | Essenfeld et al. |
| 2002/0030598 A1 | 3/2002 | Dombrowski et al. |
| 2002/0058955 A1 | 5/2002 | Blatter et al. |
| 2002/0196146 A1 | 12/2002 | Moore |
| 2003/0021021 A1 | 1/2003 | Branch |
| 2003/0119200 A1 | 6/2003 | Taft et al. |
| 2003/0122673 A1 | 7/2003 | Anderson |
| 2003/0156996 A1 | 8/2003 | Delorme |
| 2003/0233095 A1 | 12/2003 | Urbanski et al. |
| 2004/0032330 A1 | 2/2004 | Hoffman |
| 2004/0203089 A1 | 10/2004 | Fischer |
| 2005/0084425 A1 | 4/2005 | Williamson et al. |
| 2005/0100981 A1 | 5/2005 | Bjørnsen |
| 2005/0112034 A1 | 5/2005 | McCormick |
| 2005/0137272 A1 | 6/2005 | Gaserod et al. |
| 2005/0147538 A1 | 7/2005 | Williamson et al. |
| 2005/0226770 A1 | 10/2005 | Allen et al. |
| 2007/0104618 A1 | 5/2007 | Williamson et al. |
| 2007/0116612 A1 | 5/2007 | Williamson |
| 2007/0166834 A1 | 7/2007 | Williamson et al. |
| 2007/0219459 A1 | 9/2007 | Cohen |
| 2008/0138854 A1 | 6/2008 | Williamson |
| 2008/0227144 A1 | 9/2008 | Nightingale |
| 2008/0307117 A1 | 12/2008 | Muller-Cohn et al. |

FOREIGN PATENT DOCUMENTS

| | | |
|---|---|---|
| EP | 0142574 A1 | 5/1985 |
| EP | 0351988 A2 | 1/1990 |
| EP | 0357228 A1 | 3/1990 |
| EP | 0471534 A2 | 2/1992 |
| EP | 0653617 A2 | 5/1995 |
| EP | 1321757 A2 | 6/2003 |
| EP | 1967836 A1 | 9/2008 |
| GB | 865889 A | 4/1961 |

(56) References Cited

FOREIGN PATENT DOCUMENTS

| | | | |
|---|---|---|---|
| GB | 1483574 | A | 8/1977 |
| GB | 2189596 | A | 10/1987 |
| GB | 2278441 | A | 11/1994 |
| GB | 2461663 | A | 1/2010 |
| JP | 62067424 | A | 3/1987 |
| JP | 8189883 | | 7/1996 |
| JP | 11132923 | A | 5/1999 |
| JP | 2001228063 | A | 8/2001 |
| JP | 2001289755 | A | 10/2001 |
| JP | 2001296220 | A | 10/2001 |
| JP | 2006105839 | A | 4/2006 |
| KR | 100458860 | B1 | 11/2004 |
| WO | 8600407 | A1 | 1/1986 |
| WO | 00/19897 | A1 | 4/2000 |
| WO | 0109607 | A1 | 2/2001 |
| WO | 03034033 | | 4/2003 |
| WO | 03040697 | A1 | 5/2003 |
| WO | 2004028693 | A1 | 4/2004 |
| WO | 2004029584 | A1 | 4/2004 |
| WO | 2005037182 | A2 | 4/2005 |
| WO | 2007/074769 | A1 | 7/2007 |
| WO | 2008073387 | A1 | 6/2008 |
| WO | 2008112145 | A1 | 9/2008 |

OTHER PUBLICATIONS

U.S. Patent and Trademark Office, International Search Report in Corresponding PCT/US02/30779, Jan. 17, 2003, 3 pgs.
U.S. Patent and Trademark Office, International Preliminary Examination Report in Corresponding PCT/US02/30779, May 12, 2004, 3 pgs.
U.S. Patent and Trademark Office, International Preliminary Examination Report in Corresponding PCT/US02/30775, Oct 28, 2004, 12 pgs.
U.S. Patent and Trademark Office, International Preliminary Examination Report in corresponding PCT Serial No. PCT/US04/33604, May 8, 2006.
U.S. Patent and Trademark Office, International Preliminary Examination Report in Corresponding PCT/US98/20478, Sep. 3, 1999,3 pgs.
U.S. Patent and Trademark Office, International Search Report and Written Opinion in PCT Application Serial No. PCT/US10/21773, Mar. 8, 2010.
U.S. Patent and Trademark Office, International Search Report and Written Opinion in PCT Application Serial No. PCT/US09/069573, Mar. 11, 2010.
U.S. Patent and Trademark Office, International Search Report and Written Opinion in PCT Application Serial No. PCT/US07/25253, Mar. 13, 2008.
U.S. Patent and Trademark Office, Written Opinion in Corresponding PCT/US02130775, Aug. 9, 2004, 6 pgs.
U.S. Patent and Trademark Office, Office Action in U.S. Appl. No. 11/072,119, filed Dec. 19, 2008.
U.S. Patent and Trademark Office, Office Action in U.S. Appl. No. 11/072,119, filed Jul. 1, 2009.
European Patent Office, European Search Report in EP Application No. EP10193361, Apr. 18, 2011.
European Patent Office, European Search Report in EP Application No. 10177826, May 20, 2011.
European Patent Office, European Search Report in EP Application No. 08013740, Oct. 23, 2008.
European Patent Office, European Search Report in EP Application No. 06076973, Feb. 2, 2007.
European Patent Office, Official Action in EP Application No. 02773621, Dec. 3, 2008.
European Patent Office, Official Action in EP Application No. 02773621, Sep. 23, 2010.
European Patent Office, Supplementary European Search Report in EP Application No. 98951995, Dec. 20, 2007.
European Patent Office, Supplementary European Search Report in corresponding EP 02776027, Jul. 7, 2006.
European Patent Office, Supplementary European Search Report in EP Application Serial No. EP04794852, Apr. 21, 2008.
European Patent Office, Supplementary European Search Report in EP Application No. 02773621, Sep. 2008.
European Patent Office, Examination Report in EP Application No. 98951995, Jun. 18, 2009.
European Patent Office, Examination Report in EP Application No. 98951995, Apr. 14, 2008.
Sakura Finetek U.S.A. Inc., Tissue-Tek® TEC™ 5, Brochure, 2001.
Sakura Finetek U.S.A. Inc., Tissue-Tek® VIP™ 5, Brochure, 2001.
Japanese Patent Office, Office Action in Japanese Application No. 2004-539746, Aug. 1, 2007.
Japanese Patent Office, Office Action in Japanese Application No. 2004-539747, Jul. 24, 2007.
Adding RFID Layer to Blood Safety Loop, CAP Today, Article, Jul. 2005, 6 pgs.
Bar Coding for Patient Safety, The New England Journal of Medicine, 353;4, Jul. 28, 2005.
Nicholas G. Genes et al., Effect of substrate mechanics on chondrocyte adhesion to modified alginate surfaces, Archives of BiochemistryandBiophysics 422 (2004) 161-167.
The Latest in Products and Services, Bar Coding/RFID, www.healthcare-informatics.com, Nov. 2005.
Zebra'S RFID Readiness Guide: Complying With RFID Tagging Mandates, Zebra Technologies, Jan. 2004.
Australian Patent Office, Examination Report in AU Application No. 2010206709, Nov. 12, 1012.
Chinese Patent Office, Office Action in Chinese Application No. 201080005337, Mar. 5, 2013.
Japanese Patent Office, Office Action in JP Application No. 2011-548127, Aug. 27, 2013.
Europeant Patent Office, Supplementary European Search Report in EP Application No. 10733886, Jan. 17, 2014.
Chinese Patent Office, Second Office Action in Chinese Application No. 201080005337, Nov. 25, 2013.

METHOD FOR ORIENTING TISSUE SAMPLES ON A MICROTOME SECTIONABLE BIOPSY SUPPORT

This application is a divisional of application Ser. No. 12/692,208, filed Jan. 22, 2010 (pending), which claims the benefit of U.S. Provisional Patent Application Ser. Nos. 61/146,444 and 61/238,913, respectively filed on Jan. 22, 2009 and Sep. 1, 2009, the disclosures of which are expressly incorporated by reference herein. This application is also related to application Ser. No. 11/954,112, filed on Dec. 11, 2007 (pending), the disclosure of which is hereby fully incorporated by reference herein.

TECHNICAL FIELD

The present invention generally relates to supports for handling and embedding tissue samples for pathological analysis and, more particularly, to sectionable supports which can receive one or more tissue samples and be embedded and subsequently microtomed with the tissue sample or samples.

BACKGROUND

To accurately diagnose various tissue diseases and conditions, medical personnel must remove one or more samples of tissue from the body of a patient. This process of harvesting tissue from the body is known as a biopsy. Once the tissue sample or samples are removed and sent to a pathology laboratory, the tissue will go through a series of procedures performed by a histotechnician and, ultimately, a pathologist, in order to diagnose one or more conditions associated with the tissue. The present invention generally relates to those procedures that are normally performed by the histotechnician to prepare the tissue sample or samples into slides that may be analyzed under a microscope by the pathologist.

Although the singular term "sample" is used throughout this specification, it should be understood that this term likewise encompasses plural "samples" as well. Once a tissue sample is removed from the body of a patient, it is typically placed into a specimen container containing a tissue fixative solution, such as formalin, and then the container is transported to a pathology laboratory. The tissue will undergo a process known as "grossing-in" in the pathology lab during which a histotechnician will retrieve the tissue sample from the container, typically cut the tissue into appropriate sizes for tissue processing, place individual samples into the appropriate sized small plastic tissue cassettes, and assign tracking numbers to each cassette. These tracking numbers are then logged into a tracking system used in the laboratory. For the smallest tissue samples, which may only be scrapings, the cassette includes fine mesh openings on the sides and bottoms so as not to lose the samples in the processor fluids. In other situations involving very small tissue samples, the samples are placed into a bag that resembles a tea bag that prevents the smallest tissue samples from escaping. Larger tissue samples are placed into cassettes having somewhat larger slotted openings which are nevertheless smaller than the tissue sample inside the cassette.

The cassettes are then placed into a stainless steel perforated basket and run through a tissue processing machine, often overnight. This machine uses a combination of vacuum, heat, and chemicals to remove the interstitial fluids within the tissue. Once the fluids have been removed from the tissue samples, the processing machine immerses the tissues samples in a bath of a hardenable material such as molten paraffin (i.e., a form of wax) so that the interstices in the tissue are replaced with paraffin. The histotechnician then removes the basket from the machine and removes the individual tissue cassettes. In a conventional procedure practiced for many years, the histotechnician individually removes the tissue sample from each cassette. The histotechnician must carefully orient the tissue sample, based on tissue type, into a stainless steel base mold that is roughly the size of the tissue cassette and is partially filled with molten paraffin. The tissue sample must be manually held, typically using forceps, flat against the bottom of the mold. If the tissue sample is not held flat against the bottom of the mold, this could compromise the ability to make proper slices of the tissue sample later in a microtome. Long thin tissue samples present a particular problem and must be held flat over their entire lengthwise surface so that the resulting slide will contain information indicative of the entire sample. The molten paraffin is then rapidly cooled on a refrigerated plate, which may be a thermal electric cooler (TEC), to partially solidify the paraffin thereby holding the tissue sample in the proper orientation against the bottom of the mold. The cassette is then placed on top of the base mold and an embedding material, which is also typically paraffin wax, is poured through the opened top of the cassette into the base mold. The cassette changes its function at this point in the procedure from a tissue holding component to a fixture type device for mounting in the microtome and making shavings or slices from the solidified paraffin and embedded tissue using the microtome. The base mold is chilled until all of the molten paraffin has hardened and the histotechnician removes the stainless steel base mold from the block of embedded paraffin. The tissue sample is thus embedded within a rectangular block of hard paraffin with a plastic tissue cassette on the opposite side. As mentioned, the cassette may then be used as a holder or fixture in the chuck of the microtome. As with the tissue processing machine, the embedding process is accomplished in a batch fashion during which an average histotechnician may embed approximately 40 to 60 cassettes per hour.

The blocks of hardened paraffin containing the embedded tissue samples are then ready to be sliced into extremely thin sections for placement on a microscope slide. The histotechnician mounts the embedded tissue block in a chuck on the microtome that is sized to accept the side of the block that has the embedded plastic cassette. The histotechnician can then begin slicing the paraffin block which has the tissue sample embedded opposite to the plastic cassette surface. This yields a ribbon of individual slices of the tissue embedded in the hardened paraffin. The action of the microtome causes the individual slices to stick together when done properly and, subsequently, these very thin ribbons of slices are floated into a water bath and a glass slide is carefully placed underneath the slice. The slice, with the thin sectioned tissue sample embedded therein, is then adhered to the top of the slide.

When the histotechnician has enough slides from the tissue sample, the slides are placed into an automatic staining machine. The staining machine goes through a series of infiltrating steps to stain the different tissue and cells of the slide different colors. This helps the pathologist identify different structures and makes it easier to find any abnormalities in the tissue. After the staining procedure is complete, the slides are cover slipped and prepared for the pathologist to place under a microscope for analysis.

Based on the summary of the procedure provided above, it will be appreciated that conventional tissue sample handling and processing is a very labor-intensive process involving several manual steps performed by a histotechnician. Thus, repetitive stress injuries such as carpal tunnel syndrome are prevalent. This is especially true with the tissue sample embedding process. These multiple manual operations and repeated tissue handling increase the likelihood of human error and, moreover, require highly trained and skilled histo-technicians to ensure that the tissue samples ultimately adhered to the slides for analysis by the pathologist are in an optimum condition and orientation to make accurate diagnoses.

U.S. Pat. No. 5,817,032 (the '032 patent) and U.S. Pat. No. 7,156,814, and U.S. Patent Application Publication Nos. 2005/0226770; 2005/0147538; and 2005/0084425 disclose various improvements to this area of technology, including new manners of holding tissue samples during the grossing in, embedding, and microtome or slicing procedures. The disclosures of (the '032 patent) and U.S. Patent Application Publication Nos. 2005/0226770; 2005/0147538; and 2005/0084425 are hereby fully incorporated by reference herein. For example, the '032 patent relates to a tissue trapping and supporting device, which may be a cassette, and which may be successfully sectioned using a microtome. When such a sectionable cassette is used, the tissue sample is immobilized within the cassette and subjected to the process for replacing tissue fluids with paraffin. Then, the tissue sample and the cassette are sliced at the same time for later mounting on microscope slides. Because the tissue sample is never removed from the cassette from the time it is processed in the tissue processing machine to the time that it is cut or sliced with the microtome, a significant amount of handling time is saved. Moreover, the chance for human error or tissue loss is significantly reduced due to the elimination of separate tissue handling steps. The '032 patent and the above-incorporated published applications also generally disclose further improvements that help to automate the overall process and, in conjunction with the novel tissue supports (e.g., cassettes), can even further reduce the handling steps during the entire procedure and make the procedure more reliable.

Sectionable cassettes for histopathology, such as mentioned above, need to accommodate many different types of tissue. It is up to the histopathology technician to orient the tissue for processing and paraffin embedding so as to guarantee the availability of optimum diagnostic information from the eventual microscopic slide made from sections of the processed tissue. In some cases, tissue samples do not require any delicate or specific orientation for sectioning. Other tissue types require very specific orientation during the embedding process.

Standard practices for tissue orientation and embedding techniques are well known and understood in the art. The use of sectionable cassettes makes changes to some of these standard practices necessary and makes the need for more tools and devices to aid the process evident. In the process, such as that previously disclosed for sectionable cassettes, final orientation and alignment of tissues in the paraffin block are determined prior to closing the lid of the cassette and sending it through the processor. There is no opportunity for reorientation prior to paraffin embedding. This is one of the most important benefits to the automation process as the tissue is handled only once as it is placed into a cassette with no further downstream human intervention. This necessitates that the initial tissue orientation and placement in the cassette be correct and not subject to change during the process. While large samples require only moderate attention to the precision of tissue orientation, the opposite is true for small biopsies such as those produced during dermatology procedures. The pathology lab is a busy environment and throughput of tissue samples must be maintained to keep up with the case load. Automation of the histopathology lab is being implemented on a regular basis. While automation is being embraced, the inventors of this technology have had to continually make improvements and innovations to insure that the quality of the slides is not compromised by the introduction of the automation steps or devices. Any steps introduced must be cost effective and time-efficient. Therefore, the need to reduce time and steps in the process is mandatory, while the quality of the tissue sample preparation and diagnostic slide must remain extremely high.

In order for automation in the histopathology lab to be widely accepted it is imperative that all types of tissues can be embedded in sections correctly. One of the most challenging types of tissue to properly orient and embed is that of skin samples. With the increase of skin cancers all around the world, the number of corresponding diagnostic procedures that must be carried out on the biopsy samples created from skin lesion removals has increased as well. Once a skin lesion is identified for removal many different types of surgical intervention can be undertaken. One of the simplest and fastest removals is a shave biopsy. To perform a shave biopsy the lesion is first pinched by the surgeon, between his thumb and forefinger. He then takes a shallow shave cut parallel to the skin to remove the lesion. This is usually done on lesions that are less than 6 mm in diameter and in most cases only removes the top layers of the skin. Most doctors will send all biopsies to the pathology lab to confirm that there are no cancerous cells in the removed tissue. Because shave biopsies are thin and small, they are particularly difficult to orient properly in the paraffin for tissue sections. When embedded by hand, small forceps must be used to hold the thin tissue samples against the bottom of a metal paraffin mold with the proper orientation until the paraffin has cooled. It can then be difficult to remove the forceps without dislodging the tissue sample and altering its orientation. This procedure must be repeated so that all of the tissue samples from that procedure are properly embedded in the same block. If the paraffin has solidified enough to retain the first sample, it may be too solidified to accept the second sample. This sets in motion a battle between the paraffin being either too hot or too cold and the histopathology technician struggling to see through the now opaque and rapidly solidifying paraffin, trying to make sure that the second sample is properly oriented. This procedure is delicate and tedious and often produces less than optimal results.

While the shave biopsy method may be an effective and quick lesion removal for benign lesions it is not appropriate if one suspects the presence of cancerous cells. In those cases a more invasive procedure using a biopsy punch or surgical scalpel is required to remove the lesion down through the full dermis to the fat layer. This produces a thicker tissue sample which again must be properly oriented during the embedding process to create the proper diagnostic slide. For a skin biopsy to be properly oriented for diagnostic review the gross in process and embedding procedure is typically as follows. The tissue sample is removed from the biopsy transport and fixation container. The formalin solution in the biopsy container usually causes the biopsy sample to curl and become distorted. The histopathology technician must first remove the tissue from the sample container and attempt to gently flatten it on the cutting board so that the lesion can be viewed as it appeared on the patient. The tissue sample should then be transected through the lesion. The two exposed freshly cut edges will then need to be oriented parallel to the eventual microtome sectioning surface. This gives the pathologist the correct diagnostic cross-section of the lesion in which to stage any disease. It is important to understand that when diagnosing skin disease the depth of the intrusion of the disease is far more important as a measure of its invasiveness than is the diameter on the surface of the skin. That is why it is so important to have the proper cross-section view of each lesion to be able to assess how far into the skin layers cancer cells have penetrated. Therefore, any device which is intended to enhance or enable the tissue orientation process for automated embedding must preserve these very specific orientation requirements in order to be useful.

With specific regard to prior art devices designed by this inventor, novel improvements have been made from disclosures in U.S. Pat. No. 7,156,814 which render far superior results in the case of tissue handling and orientation, tissue processing, paraffin embedding, microtome sectioning, slide preparation and, finally, diagnostic usefulness.

Note that while embodiments in this disclosure are primarily directed toward tissue orientation and holding alignment devices for use with sectionable tissue embedding cassettes and automated systems, the orientation device itself can be manually embedded in a paraffin block and sectioned along with the tissue without the use of an automated embedding machine or process. Therefore, no limitation should be construed upon the orientation device for use only with sectionable cassettes.

Small, thin samples like those derived from skin shave biopsies or needle biopsies are too thin and elongated to be held in place by a single pincher point. The tissue needs to be supported along its longest axis to prevent it from curling and pulling away from the sectioning plane. In the prior art it was very difficult to orient and retain the samples all on the same sectioning plane.

One of the challenges encountered with devices in the '814 patent, such as those disclosed in FIGS. 78a-80, is the procedure for gripping the tissue prior to its placement in a cassette. The '814 disclosure taught holding the tissue on edge and placing the orientation device over top of it. This proved to be problematic in situations where the tissue has no intrinsic strength to hold its own shape. It is also a problem when the tissue samples are extremely small and human dexterity is challenged working with those sizes. Other important hurdles to overcome include the potential for of crush artifact in the tissue, which can impede diagnosis, and the potential for air bubbles in the embedding material, which can impede high quality ribbon slices. In the past, these concerns have competed with the goal of accurately orienting and retaining the original presentation and orientation of the tissue sample throughout processing and embedding. Clearly, a more user-friendly solution is needed.

In spite of the various advances made in this field, there is an increasing need for additional improvements related to increased production capability and more consistent quality of embedded tissue samples and resulting slices or ribbons of embedded tissue that will be subject to diagnosis. This can be especially important when handling smaller tissue sample sizes, such as very small elongated tissue samples produced from coring or needle biopsy instruments. In addition some tissue samples like skin lesion biopsies must maintain special orientation throughout tissue processing and embedding steps. Although the improvements to be disclosed herein are applicable to any tissue sample sizes, there are specific biopsy samples which regardless of their size must maintain either proper orientation or extreme flatness to allow for diagnostically correct sections to be obtained for the production of microscope slides. Core biopsy tissue samples present a particular challenge in keeping the entire core sample held flat along its entire length in the tissue supporting structure. This challenge is exacerbated by the actual core sample harvesting process. Currently, the practitioner, most often a radiologist, performs the core biopsy procedure with a needle. After harvesting, the core sample is ejected from the needle directly into a bottle containing a solution of buffered formaldehyde or formalin. This solution "fixes" the tissue. The fixing process preserves the tissue and prevents degradation and contamination, but also hardens the tissue and causes the tissue to curl up as it contracts due to the interaction with the formalin. This curl artifact is highly undesirable because the tissue needs to be held flat while it is embedded in the paraffin. There is a significant need for improvements designed to straighten and hold the core sample flat during the embedding process.

SUMMARY

In one general embodiment, a histologic tissue sample support device is provided and may generally comprise a tissue cassette coupled with a tissue biasing lid which incorporates holding tabs, and/or other types of tissue sample biasing structure such as a resilient cellular material. The tissue cassette is specifically designed to orient very small, elongated tissue samples, and hold these samples securely throughout processing. The tissue sample support device can more specifically include a tissue cassette formed of material which can be successfully sectioned in a microtome and is resistant to degradation from solvents and chemicals used to fix, process and stain tissue. Any of the features disclosed in the above-incorporated disclosures may be included in the embodiments disclosed herein.

In the preferred embodiment, an adjustable lid is used to bias the tissue samples down towards the bottom inside surface of the tissue cassette. The biasing tabs on the lid or other biasing structure(s) integrated into the lid or otherwise in the cassette hold the tissue firmly against the bottom surface so that the entire lengthwise extent of the tissue is held in a single sectioning plane. In addition, all of the samples inserted into this type of cassette are held on the same plane. Typically, core samples are taken from different physical quadrants or sample areas of a suspected lesion or organ and it can be important to be able to associate each with its origination location. The cassette includes physical barriers or separating structure between the channels or troughs that hold the samples to maintain sample segregation and origination information. The separating structure in the base of this tissue cassette create discrete channels or troughs to make certain that the samples do not switch places or migrate during the processing and paraffin embedding steps. This separating structure is perforated to allow infiltration of processing fluids and embedding material. The separating structure maintains the same tissue placement throughout processing, embedding and slide preparation. This is important because anomalies may appear in one area of an organ and not in another and therefore origination information for each sample is required so that relevant diagnostic information can be taken from the biopsy. The preferred embodiment has four discrete channels or troughs which keep four elongated tissue samples separated. In one embodiment, one or more anchoring elements are associated with the separating structure and include at least one surface facing the bottom wall of the cassette. This surface engages embedding material to resist the pulling or chipping out of the separating structure during sectioning. In another embodiment resilient fingers are provided on opposite sides of the channels. The fingers face each other and may be biased outwardly away from each other to receive variously sized tissue samples in a precisely oriented and firmly held manner. The fingers may be formed in a one-way barbed-type manner to prevent the tissue sample(s) from moving back out of the channel. The separating structure may be interrupted in one or more locations or otherwise configured to allow a more elongated sample to be wrapped or extended from one channel to the next adjacent channel.

It is not only important to retain origination information for each sample in the microtome sectionable tissue cassette, but the eventual paraffin block must be easily sectioned in a microtome to provide samples for microscopic analysis and diagnosis. When done properly, as each slice is made with the microtome, it attaches to the next slice making a ribbon which can be floated on water in order to easily capture each slice onto a microscope slide. The ribbon will fail to form properly if the free bodies of plastic which support the tissue are allowed to be dislodged or "chipped" out from the block by the action of the microtome. The internal separating structure of this preferred embodiment is an improvement that enables the tissue to be segregated and sectioned without ribbon destruction. The same problem exists with very small core samples that can chip out of the paraffin slice. The internal structure provided by the interconnection of the four channels in the preferred embodiment offers an improvement in the handling of these small core samples. They are less likely to chip out and destroy the ribbon when surrounded by this interconnecting structure, including anchoring structure, which becomes firmly held in the paraffin block with the tissue sample.

In another embodiment, a resilient cellular material is used alone or in addition to the biasing tabs on the lid of the cassette to insure that small pieces of tissue, and tissue of different size and/or shape can be immobilized in the channels throughout the tissue processing and embedding. In some cases where the core biopsy samples are very small in diameter or are fragmented as a result of the extraction process, it is necessary to provide further insurance against tissue migration by placing a resilient cellular material between the lid of the cassette and the tissue sample. This resilient cellular material allows free flow of processing fluids and paraffin to the sample while maintaining a biased orientation of the tissue sample against the bottom surface of the cassette. The porosity of the resilient cellular material allows infiltration of the solvents and chemicals used to fix, process and stain tissue, and of embedding material used to embed the tissue while the tissue is retained by the resilient cellular material. The resilient cellular material is compressible and configured to engage and retain tissue in place during processing and embedding and is also capable of successful sectioning in the microtome after having its interstices or pores filled with liquefied embedding material (e.g., paraffin) which subsequently hardens. The resilient cellular material may further comprise an open cell foam material, such as a foam including at least one of a polyether or a polyurethane. In addition, the open cell foam may be a fully reticulated foam. This helps ensure full infiltration of fluids used during processing and embedding procedures. Other synthetic and natural materials may be used such as polyesters, alginates, or other materials that may be infiltrated with the embedding material and successfully sectioned with a microtome without adverse effects on the resulting ribbon of tissue and embedding material.

The interior area of the tissue cassette may be configured to at least partially contain the resilient cellular material either during the manufacturing of the cassette or the cellular material may be inserted into the recess or interior area by the user in order to retain the tissue sample in place during processing and embedding procedures. In one embodiment, the resilient cellular material is coupled to the lid and is inserted at least partially into the containment portion upon connecting the lid to the containment portion.

As mentioned, an embodiment provides channels with sectionable fingers on opposite sides along the length of each channel to hold a tissue sample such as a skin lesion upright or otherwise in a proper orientation. These fingers are preferably resiliently biased normally toward the center of each channel so as to hold the sample(s) firmly therebetween. In one example, a skin lesion is excised and then sliced in half longitudinally. The cut edge is oriented parallel to the sectioning plane within a channel so that the depth of the lesion can be determined within a single slide for diagnosis. The biasing structure, previously mentioned, such as tabs protruding from the lid or resilient cellular structure hold the sample down within the channels. The structure forming the channel or trough provides support for the tissue on opposite sides such as through the use of the fingers that hold the tissue in the desired orientation throughout processing and embedding.

The material forming the cassette may be at least translucent, if not transparent, so as to be non-distracting during tissue analysis. For example, the microtome sectionable tissue sample cassette may be formed of any suitable sectionable material such as any of the materials disclosed in the above incorporated patent and patent applications such as polymers including fluorinated polymers or fluoropolymers (e.g., PFA or FEP).

An assembly may be constructed with the cassette and a separate frame. In such an assembly, the tissue cassette is releasably retained on the frame and the frame is further configured for releasable securement within a microtome chuck. The frame can further include an interior and the tissue cassette may be sized to fit and move within the interior between at least a first position and a second position. The first position is used during processing of the tissue sample, and the second position is used to expose the tissue outward of the frame in a position for allowing the tissue support, tissue sample and hardened block of material such as paraffin to be sectioned in the microtome.

Various methods are disclosed or will be apparent based on a review of the disclosed embodiments and features. For example, a method for preparing one or more biopsy tissue samples for histological examination may generally comprise:

positioning a tissue sample in close proximity to a microtome sectionable support;

biasing the tissue sample towards the inside bottom surface of a tissue support;

immobilizing the tissue sample on the support by contacting the tissue sample with a microtome sectionable biasing structure which may include a resilient cellular material;

subjecting the microtome sectionable support, sample biasing structure and the tissue sample to a process that replaces fluid in the tissue sample with a hardenable material;

embedding the microtome sectionable support, biasing structure and the tissue sample in an embedding material;

hardening the embedding material into a block; and slicing the block with a microtome into thin slices of the embedding material, the microtome sectionable support, the biasing structure and the tissue sample.

The hardenable material and the embedding material may be the same material, such as a wax (e.g., paraffin). The support may further comprise a bottom portion configured to hold the tissue sample and a lid with biasing elements and alternatively including a resilient cellular material. The step of immobilizing the tissue sample can further comprise closing a lid on top of the tissue sample to trap the tissue sample between the biasing structure and the bottom portion. The bottom portion can include an interior space surrounded by at least one side wall and the positioning and immobilizing steps and can further comprise placing the tissue sample within the interior space, and inserting a resilient cellular material at least partially into the interior space and into contact with the tissue sample. The resilient cellular material may deform during the immobilizing step to create a three dimensional space that receives the tissue sample. This can help immobilize the tissue sample in a desired form flat against the bottom of the support or cassette. The force of the resilient cellular material against the tissue should be enough to immobilize and/or flatten the tissue but not enough to induce artifacts in the sample. The microtome sectionable support or cassette may be coupled to a frame prior to being subjected to the process for replacing fluid in the tissue sample with the hardenable material. The method can then further comprise securing the frame in the microtome prior to slicing the block. Prior to embedding the microtome sectionable cassette or support, resilient cellular material and the tissue sample in the embedding material, the microtome sectionable support may be moved from a first position within the frame to a second position in which the support, resilient cellular material and tissue sample are exposed for simultaneous sectioning in the microtome.

A microtome sectionable tissue orientation device is also provided that has features that secure it in the well or containment portion of a sectionable cassette with a snap or friction fit and the tissue can be placed into the orientation device while it is in the cassette well. This facilitates the handling of the sample and devices. The proper embedding of small tissue samples is a painstaking and exacting procedure. By placing the tissue orientation or alignment device inside the cassette well, the entire cassette can be fixed or held while both hands of the histotechnician or other user are available then to orient and place the tissue between holding legs of the orientation device. One effective way to assure accurate orientation of thin tissue samples such as skin biopsies, as envisioned in this disclosure, is to place them in close proximity to sectionable holding legs. Use of a sectionable insert in the form of the tissue orientation or alignment device placed and securely held in a sectionable cassette before securing the tissue sample is easier than the prior method of trying to couple the tissue to a tissue orientation device before loading the orientation device into the cassette.

In an illustrative embodiment, the tissue orientation device is locked into the cassette side walls to insure its secure location in all axes. The device is preferably oriented such that the tissue is spaced from the edges of the cassette walls. If the orientation device is not spaced away from the side walls, the possibility of air entrapment exists or the edges of the paraffin block can break-away from the main block ruining the section ribbons as a result. The orientation device has been configured so as to provide a pre-load against the inner cassette walls to hold it sufficiently secure inside the cassette away from the cassette walls during tissue processing and paraffin embedding. The closure of the lid then holds the orientation device securely against the bottom of the cassette. The additional step of closing the lid makes certain that the oriented tissue is held flat against the bottom inside surface of the cassette well. This is important because this will be the first sectioning plane once the bottom of the cassette has been sliced off by the microtome.

In one embodiment, the tissue orientation device has tissue engaging teeth on the holding legs. These teeth hold the tissue between the legs and allow the technician to more easily release the tissue from the forceps after the tissue has been forced between the holding legs. Also, the tissue becomes desiccated in the processing step. In almost all cases, this means the tissue will shrink in size. The tissue engaging teeth will hold the tissue in place between the holding legs even as it shrinks, preventing the tissue from floating free. The orientation devices may be formed of the same material as the cassettes of this invention.

Various additional details, features, advantages and aspects of the invention will become more readily apparent to those of ordinary skill in the art on review of the following illustrative, more detailed description.

BRIEF DESCRIPTION OF THE DRAWINGS

FIG. 27A is a top view of the tissue orientation device of FIG. 27 holding tissue samples.

DETAILED DESCRIPTION OF THE ILLUSTRATIVE EMBODIMENTS

The various embodiments of tissue cassettes, supports or orientation devices are especially helpful when histotechnicians work with especially small, delicate samples that are important to precisely orient during the histopathology process. One type of biopsy with such concerns is a needle biopsy. Because needle biopsies are far less invasive than those obtained through surgery and they provide an early diagnosis of disease, they have become extremely popular in today's medicine. A significant portion of diagnostic biopsies are performed using a needle biopsy device. Because needles can be made long and thin, many of the body's organs or pathology can be reached through percutaneous radiographically guided procedures. Needle core biopsies are routinely obtained in diagnostic procedures such as prostate, cervix, liver, and thyroid. Such devices are constructed to cut and retain a core sample within the interior bore of the hollow metal needle. The core sample is subsequently ejected and placed in formalin for transport to the lab. Because the samples are very long and thin they tend to curl and kink when fixed in the formalin solution. If these long snakelike biopsies are not flattened properly against the bottom of the tissue support prior to sectioning, small portions of the biopsy may go unexamined in the final diagnostic slide because they can reside in the paraffin block above the sectioned area.

Core biopsy devices are most commonly designed around a 16 gauge needle. Using ultra thin wall, stainless hypodermic tubing, the inside diameter of a standard 16 gauge would yield a sample cut to 0.055 inches in diameter. While it is fully anticipated that samples will be both smaller and larger in diameter, this is on average one of the most widely used core biopsy sample sizes. Extremely small core biopsies such as those smaller than 0.020 inches may require special handling and utilization of resilient cellular material to hold the tissue samples against the bottom sectioning plane of the cassette.

Figures 1, 2:
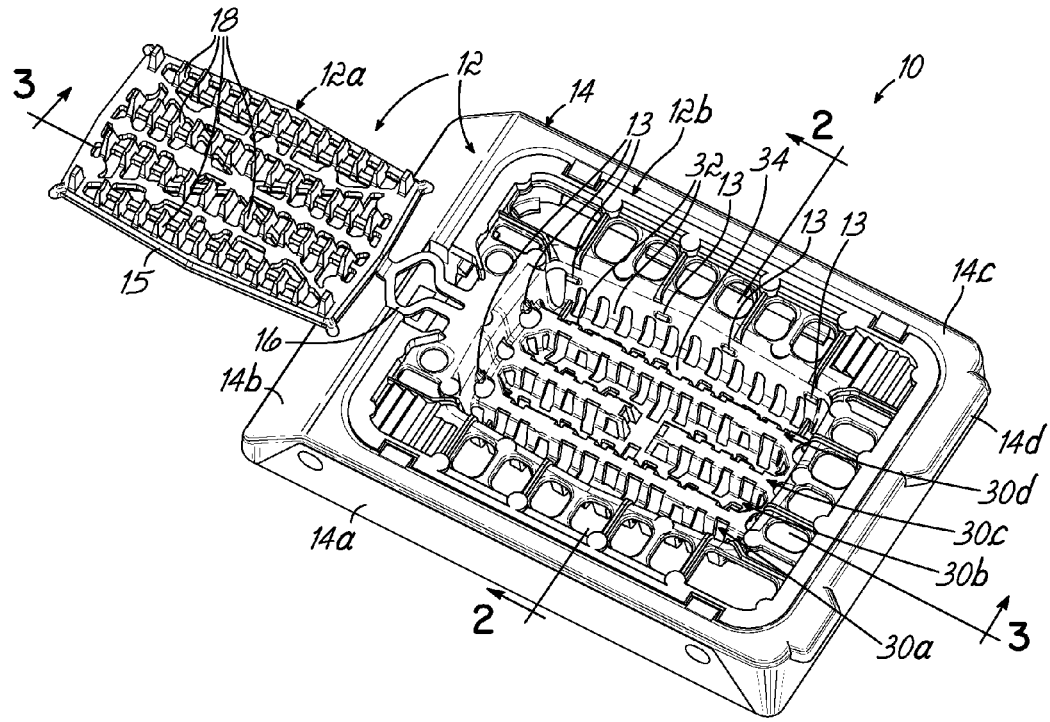
FIG. 1 is a perspective view of an assembly comprised of a microtome sectionable tissue cassette received within a frame, with the lid of the cassette shown in an open position.
FIG. 2 is a cross sectional, perspective view generally taken along line 2-2 of FIG. 1.

FIGS. 1 and 2 generally illustrate an assembly 10 comprised of a tissue sample cassette 12 carried within a frame 14. The connection of the tissue cassette 12 to the frame 14 may be accomplished in many different manners, such as any of the manners described in the above-incorporated patent and patent applications. It will also be appreciated that the cassette 12 may be configured in any suitable manner as a tissue support and the frame 14 may be configured in any suitable manner. Any of the configurations, features, characteristics and materials disclosed for the tissue supports (e.g., cassettes) and frames in the above-incorporated patent and patent applications may be employed for cassette 12 and frame 14. In the embodiment shown, the cassette 12 is porous or perforated and is releasably retained in the frame 14 and the frame 14 is further configured to be releasably secured within a microtome chuck (not shown). The frame 14 generally includes an interior defined between surrounding outer walls 14a, 14b, 14c, 14d and the cassette 12 is sized and configured to frictionally or "snap" fit and move within the interior between at least first and second positions, again, as generally discussed in the above-incorporated patent and patent applications and for the same purposes.

Figure 3:
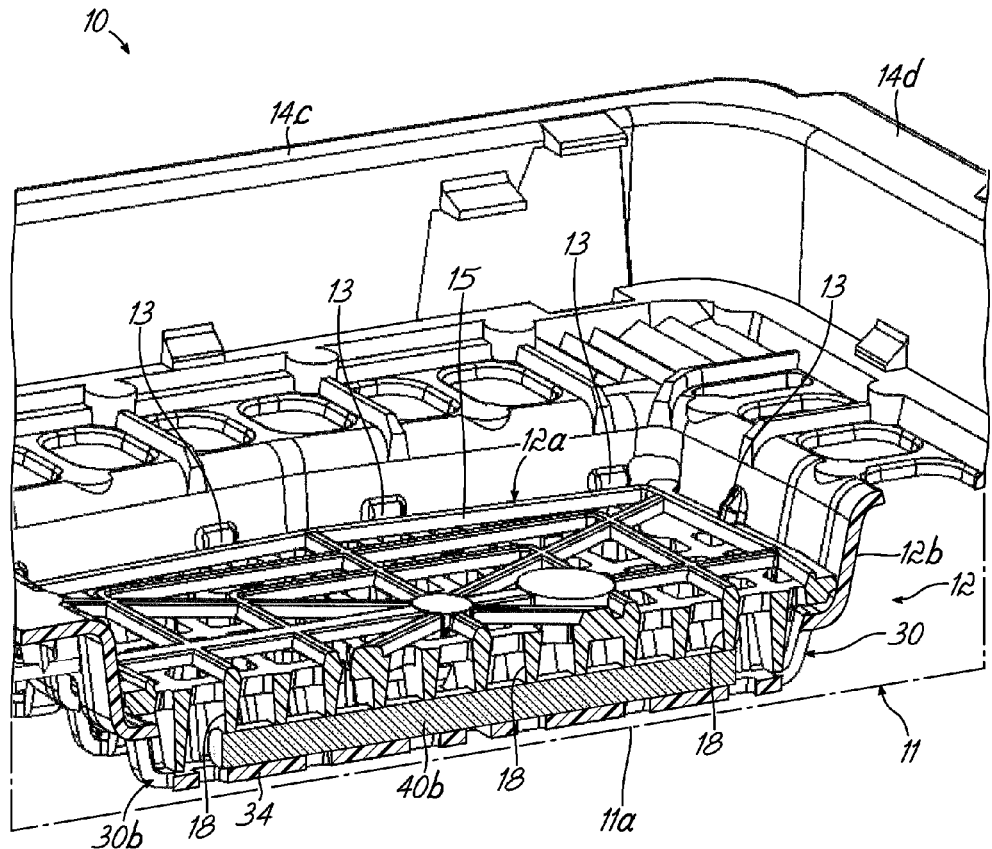
FIG. 3 is a cross sectional, perspective view generally taken along a line perpendicular to line 2-2 of FIG. 1, and showing the cassette in a second, exposed position relative to the frame for embedding and sectioning.

The first position of the cassette 12 is shown in FIG. 1, while the second position is a position in which the lower portion or well of the cassette 12 is exposed below the bottom of the frame 14, as viewed in FIG. 3, for allowing the cassette 12, tissue sample and paraffin block 11 to be sectioned in a microtome while the frame 14 is held in the microtome chuck. The general procedure for processing, embedding, and sectioning is discussed in the above-incorporated patent and patent applications. The cassette 12 and other microtome sectionable structures described herein may be formed from perfluoroalkoxyethylene (PFA) in accordance with the above-incorporated patents and patent applications.

A lid 12a of the cassette 12 may be coupled to a body 12b of the cassette 12 by a hinge 16. The lid 12a may also snap fit into a closed position as shown in FIG. 2 through engagement of fingers or projecting connectors 13 on the cassette body 12b with an outer flange 15 of the lid 12a on each of the four sides of the lid 12a. The lid 12a carries flexible, biasing tabs 18 and a resilient cellular material 20 (FIG. 6) which may, for example, be an open cell foam material, such as a foam including at least one of a polyether or a polyurethane and which may be a fully reticulated foam. Here, "fully reticulated" means that at least substantially all cells of the foam are open. Such a foam is disclosed in U.S. patent application Ser. No. 11/954,112, filed on Dec. 11, 2007, the disclosure of which is fully incorporated by reference herein. As shown in FIGS. 2 and 3, one or more elongated tissue samples 40a, 40b, 40c, 40d may be placed in porous or perforated tissue channels or troughs 30a, 30b, 30c, 30d that may define a recess or interior area bounded by separating structure on each side in the form of sidewalls 32 and including a bottom wall 34. As further shown in FIG. 2, respective sidewalls 32 are connected with top walls 33. These top walls 33 provide anchoring elements in the hardened block 11 of embedding material (e.g., paraffin) during the microtome sectioning process. That is, as understood from the microtome-ready condition of assembly 10 shown in FIG. 3 in which the microtome bladed will be moving parallel to the bottom walls 34, these bottom walls 34 are initially sliced or "faced" off and the sidewalls 32 and samples 40a-d are then sliced in conjunction with thin ribbon slices of the hardened paraffin 11. The sidewalls will be firmly retained in the block of paraffin as a result of the anchoring function provided by the more deeply embedded top walls 33 that are integrally connected with the respective sidewalls 32. The underside or surface of top walls 33 will engage the hardened paraffin thereby preventing the top wall 33 and sidewalls 32 from pulling out of the paraffin during sectioning. If portions of the cassette pull or chip out during sectioning, these portions of cassette material can severely damage or even destroy the tissue sample(s). The anchoring element (walls 34 in this example) prevents the sidewalls 32 from "chipping out" or otherwise degrading the quality of the thin, ribbon slices being taken of the cassette 12, hardened paraffin 11 and the samples 40a-d. It will be appreciated that bottom wall 34 may have discrete sections as shown in FIG. 3, associated with each channel, or may be continuous as later shown and described.

In use, the one or more tissue samples 40a, 40b, 40c, 40d are placed within the interior channels 30a-d. The cassette lid 12a is then closed and snapped into place such that the tabs 18 and, optionally or alternatively, resilient cellular material (e.g., foam) 20 (FIG. 6) bears against and traps the tissue samples 40a-d against the bottom wall 34 as shown in FIG. 2. At this point, the assembly 10 with the trapped tissue samples 40a-d may be subjected to a conventional tissue processing operation that uses vacuum, heat and chemicals to remove the interstitial fluids within the tissue samples 40a-d and replace those fluids with a hardenable material, such as molten paraffin. As mentioned above, during these processing steps, the porous nature of the foam or other resilient cellular material 20 (FIG. 6), if used, allows the fluids to reach and fully infiltrate into the tissue samples 40a-d. In addition, the foam 20 traps the tissue samples 40a-d flat against the bottom wall 34 without leaving artifacts or markings on the tissue that might interfere with subsequent analysis under a microscope. It will be appreciated that different types of resilient cellular materials may be chosen based, for example, on the type of tissue to be processed and analyzed. For example, small mucosal tissue samples may be held and processed with success using the T-50 foam discussed in the above-incorporated disclosure of U.S. Ser. No. 11/954,112, while other types of tissue, such as fatty tissue, may be better served by another type of resilient cellular material.

It will also be appreciated that the processing steps may take place before assembling the tissue cassette 12 with the frame 14. After the tissue processing is complete, the tissue cassette 12 may be moved to a second position as shown in FIG. 3 exposing the containment portion 30 below the bottom surface 14e of the frame 14. The cassette 12 and frame 14 are then placed into a suitable mold (not shown) and embedded in paraffin, such that the entire assembly including the lower exposed containment portion 30 are embedded within a hardened block 11 of paraffin wax. The mold (not shown) may generally follow the contour of the bottom of the cassette 12, although the portion of the mold surrounding the containment portion 30 is preferably square as opposed to round. This assists with the subsequent production of ribbon slices. This portion of the procedure may therefore be similar to that disclosed in the above-incorporated disclosures. As discussed therein, the frame 14 is then used as a fixture for mounting the embedded assembly 10 in a microtome chuck and the necessary number of slices are taken of the exposed underside 11a of the block 11 (FIG. 3) until enough sections are taken to reach the samples 40a-d. The microtome slices or ribbons containing the tissue samples are appropriately mounted on a microscope slide, stained and cover slipped.

Figure 4:
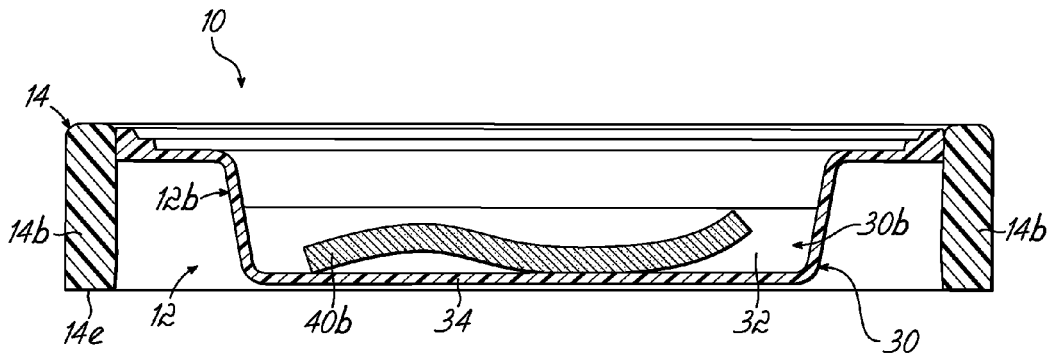
FIG. 4 is a schematic cross sectional view taken generally along the same direction as FIG. 3 and showing the elongated tissue sample positioned on the bottom of the cassette or tissue support without tissue sample biasing structure shown.

FIG. 4 is a schematic cross sectional view that illustrates an elongated tissue sample 40b positioned with a channel or trough 30b of the cassette 12. The tissue sample 40b is shown before it has been held or retained flat against the interior bottom surface of the channel 30b.

Figure 5:
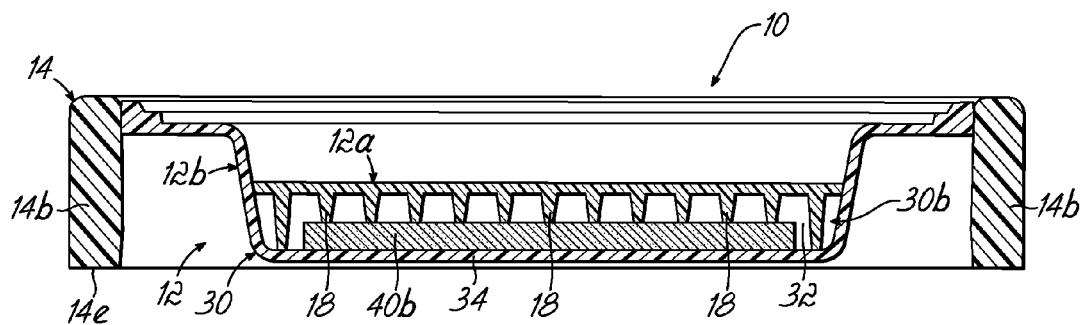
FIG. 5 is a schematic cross sectional view similar to FIG. 4, but showing the cassette lid closed and further showing its protruding tabs biasing against the elongated tissue sample.
Figure 6:
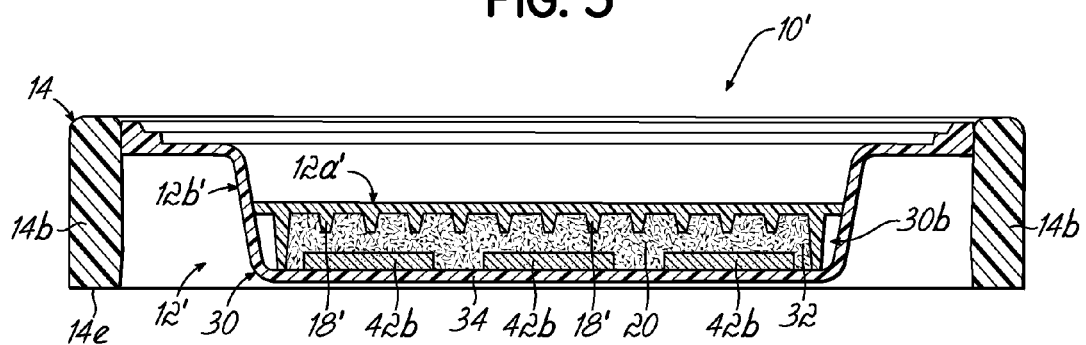
FIG. 6 is a schematic cross sectional view similar to FIG. 5, but illustrating a resilient, open celled material, such as foam, bearing against the tissue samples.

FIGS. 5 and 6 respectively illustrate two different embodiments of the cassette 12 and 12'. Cassette 12 includes only tabs 18 to engage and hold the tissue sample 40b against the bottom interior surface of the channel 30b. Cassette 12' includes somewhat shorter tabs 18 which engage resilient cellular material, such as open cell, fully reticulated foam 20, with the foam then engaging or contacting elongated tissue samples 42b contained in channel 30b. Optionally, tabs may be completely eliminated and only the resilient cellular material used to bias and hold the tissue sample(s) flat against the bottom wall 34 of the cassette.

Figure 7:
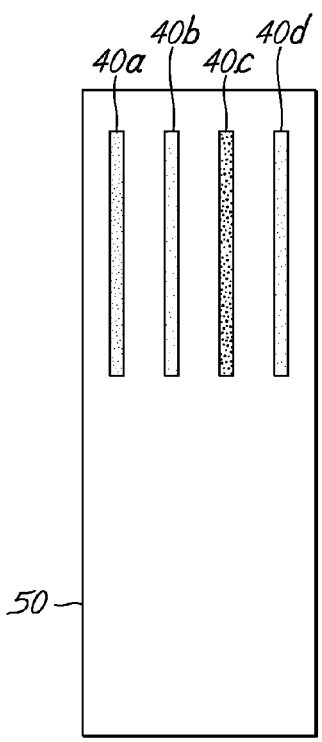
FIG. 7 is a top view of a diagnostic slide showing a section of the resulting paraffin block produced when the support in FIG. 2 is processed, embedded in paraffin, and microtome sectioned.
Figure 8:
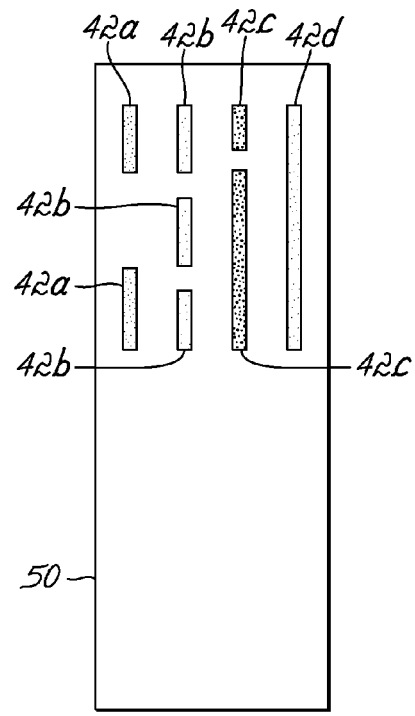
FIG. 8 is a top view of a microscope slide showing a section of the resulting paraffin block produced when the support of FIG. 6 with small fragments of tissue samples is processed, embedded in paraffin, and microtome sectioned.

FIGS. 7 and 8 respectively show microscope slides prepared with sectioned tissue samples 40a-d and 42a-d from the cassettes 12 and 12' illustrated in FIGS. 5 and 6. It will be noted that the cross-sectional view of FIG. 6 is taken through samples 42b, while the microtome sectioning occurs in a plane perpendicular to this, i.e., parallel to the plane of the bottom wall 34.

Figure 9:
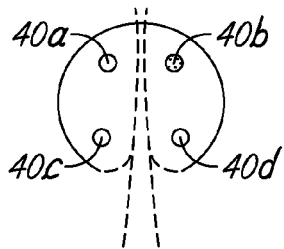
FIG. 9 is a cross sectional view of a prostate gland from which elongated core samples are obtained.

FIG. 9 is a schematic cross sectional view of a prostate gland from which elongated tissue samples 40a-d are obtained from four separate quadrants as depicted by the small circle areas in FIG. 9. These quadrants and corresponding samples 40a-d may be marked on assembly 10 for diagnosis purposes.

Figure 10:
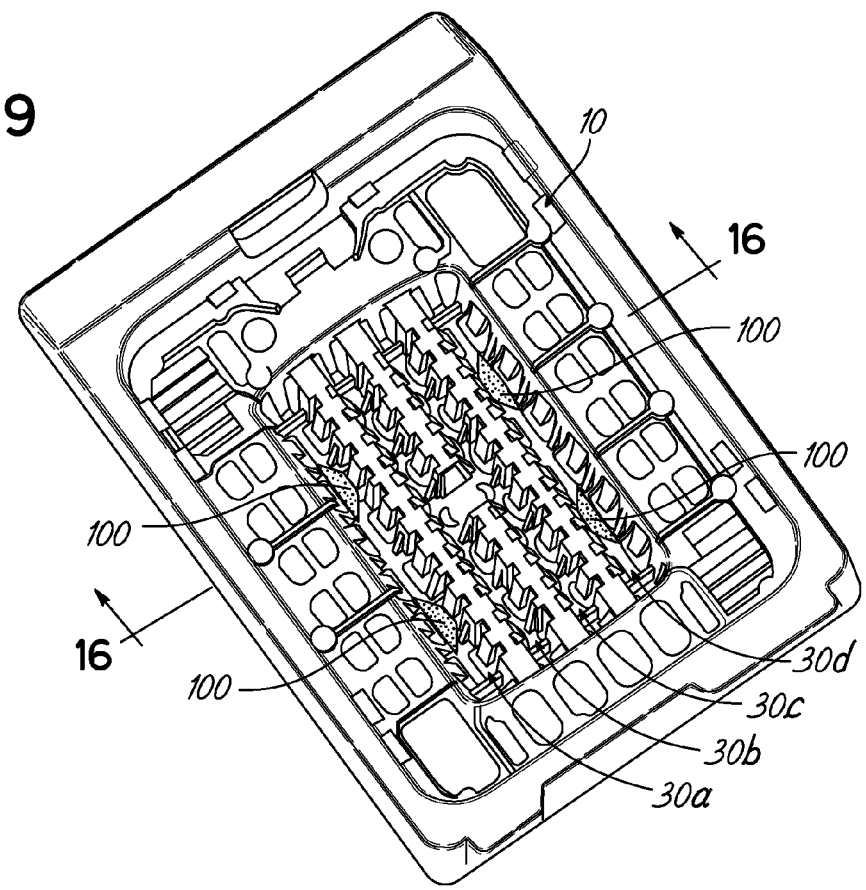
FIG. 10 is a top perspective view of a tissue cassette with the lid not shown and four channels or troughs orienting and supporting skin samples throughout tissue processing and embedding.

FIG. 10 illustrates the cassette 12 with four half-cone shaped tissue samples 100 depicted in two of the channels 30a-d alongside the outer walls of the cassette 12.

Figure 11:
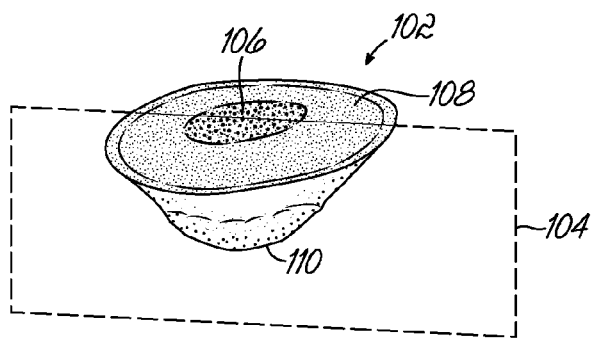
FIG. 11 is a stylized approximation of a skin biopsy tissue sample shown in perspective.

FIG. 11 depicts a stylized approximation of a skin biopsy tissue sample 102 showing the manner in which the half-cone shaped tissue samples 100 of FIG. 10 are obtained. Specifically, the lesion or tissue sample 102 shown in FIG. 11 is cut along a central plane 104. A lesion 106 is shown centrally located in the epidermis or outside layer 108 of the skin. Deeper layers of the skin and fat 110 are at the pointed or converging end of the inverted cone-shape. The lesion 106 is transected during the gross-in process before inserting the tissue sample 100 into the tissue support channel 30a or 30d as shown in FIG. 10.

Figure 12:
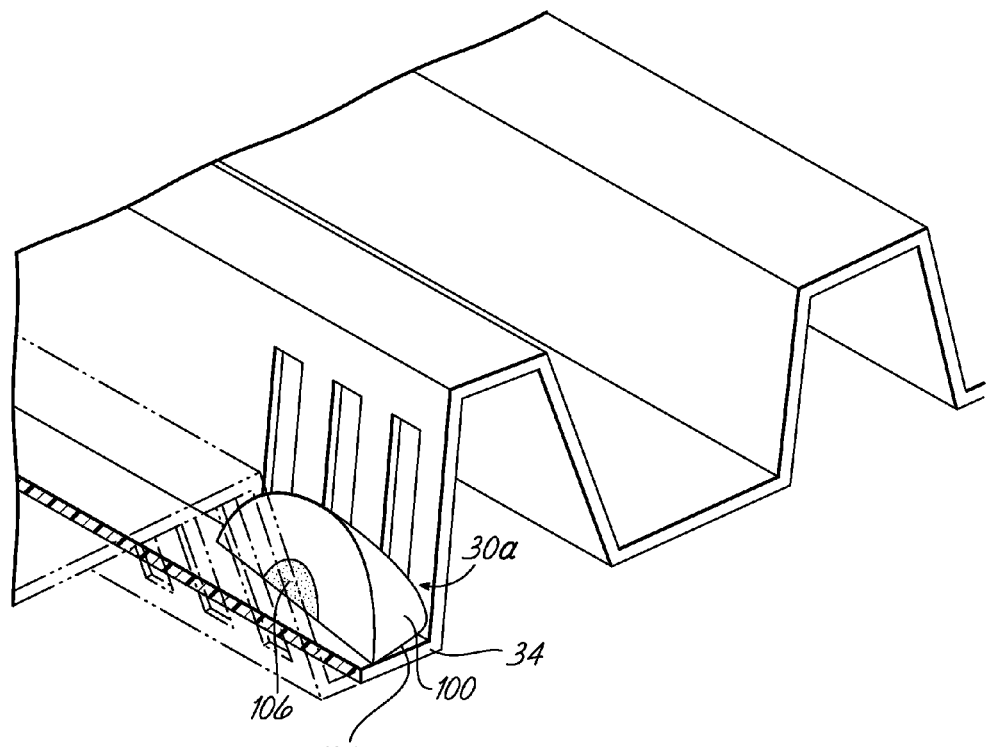
FIG. 12 illustrates one half of the transected lesion and skin sample of FIG. 11 with the cutting plane generally parallel to the bottom surface of a channel in the tissue cassette.

FIG. 12 is an enlarged view of the transected tissue sample 100 with the surface 104a formed along the cutting plane 104 lying flat against the bottom wall 34 of the tissue support channel 30a.

Figure 13:
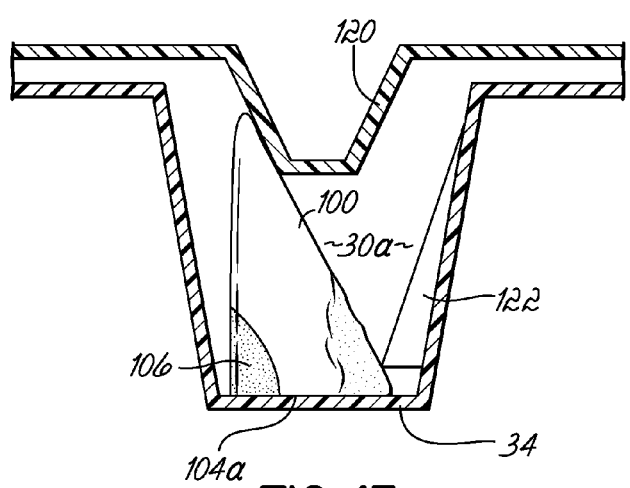
FIG. 13 illustrates an end view of FIG. 12 showing the section plane and the skin tissue sample.

FIG. 13 illustrates an end view of FIG. 12 showing the tissue sample 100 engaged by a flexible tab member 120 and flexible, opposing finger(s) 122 to hold the tissue sample 100 and, specifically, the section plane thereof firmly against the interior bottom surface of the channel 30a.

Figure 14:
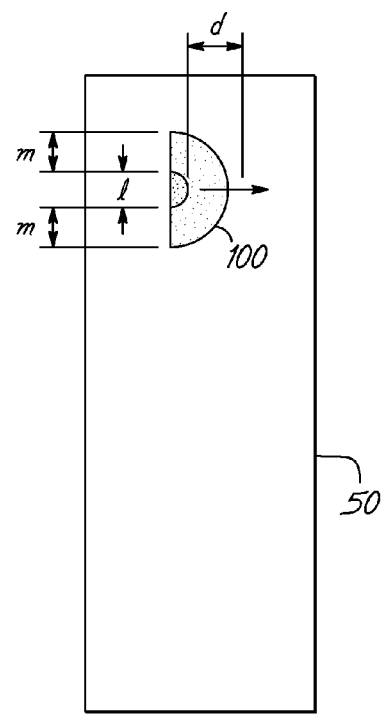
FIG. 14 illustrates a microscope slide made from sectioning the skin tissue sample as shown in FIG. 13 after the cassette has been processed, embedded in paraffin, and microtome sectioned.

FIG. 14 illustrates a microscope slide made from a microtomed section or slice of the cassette illustrated in FIG. 13, after the cassette and tissue sample 100 have been processed, embedded and microtomed according to the discussion above. The sectioned sample 100 is illustrated in a manner showing the margins "m" of the lesion"l" and the depth "d".

Figure 15:
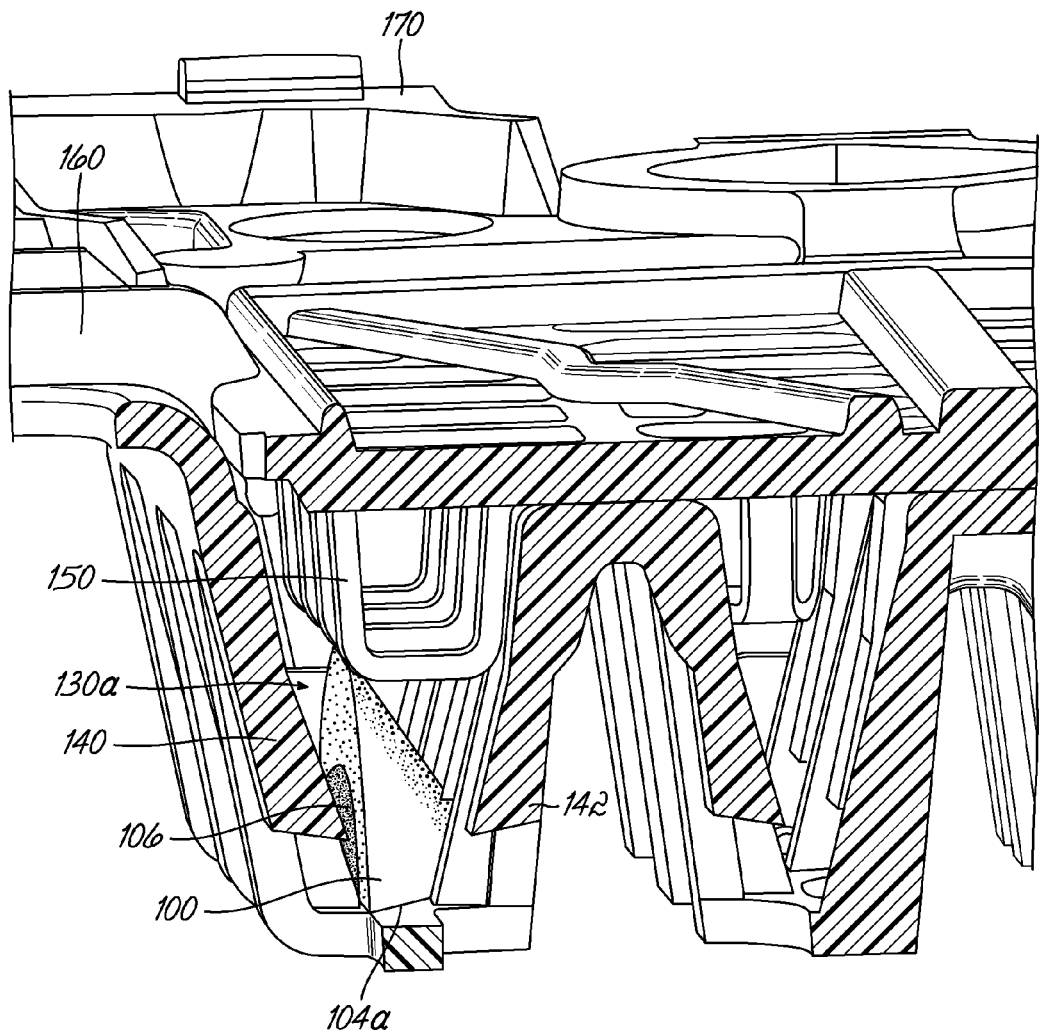
FIG. 15 is an enlarged, cross sectional perspective view of a portion of FIG. 16 with the lid shown in place.
Figure 16:
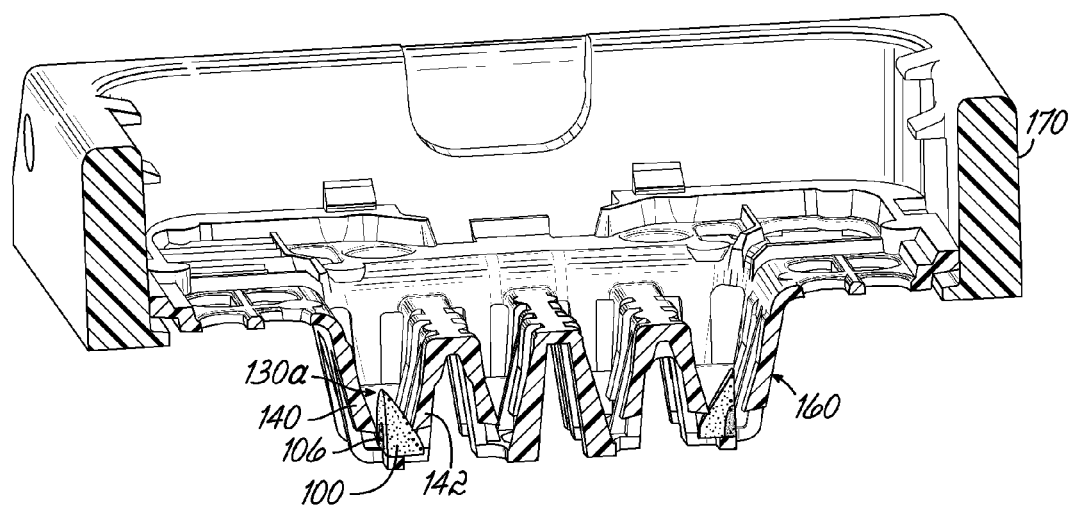
FIG. 16 is a cross sectional, perspective view taken generally along line 16-16 of FIG. 10.

FIGS. 15 and 16 are perspective sectional views illustrating the tissue sample 100 of FIG. 13 placed in a channel 130a and the alternative use of cantilevered and, preferably resilient, fingers 140, 142 biased toward each other on opposite sides of the channel 130a. These fingers 140, 142 serve various functions. During insertion of the tissue sample 100 down into the channel 130a using forceps, the fingers 140, 142 grip the tissue sample 100 to keep it from moving back out of the channel as the user is placing and orienting it. The fingers 140, 142 are shown with a one-way barbed configuration for this purpose and for accurately and reliably maintaining the original presentation and orientation of the tissue sample 100, as established by the user during placement, throughout the remainder of the processing and embedding operations. The resilient fingers 140, 142 can accommodate tissue samples of various sizes in this manner. In addition to the fingers 140, 142, lid tabs 150 and/or other biasing structure hold surface 104a of the sample 100 biased against the lower or bottom interior surface of the channel 130a. FIG. 15 illustrates an enlarged view of one of the channels 130a holding the tissue sample 100, while FIG. 16 illustrates a similar view showing the entire cassette 160 held within a frame 170 and in the lower or outer position of the cassette 160 relative to the frame 170 exposing the cassette 160 for embedding and microtome sectioning purposes as previously discussed.

Figure 17:
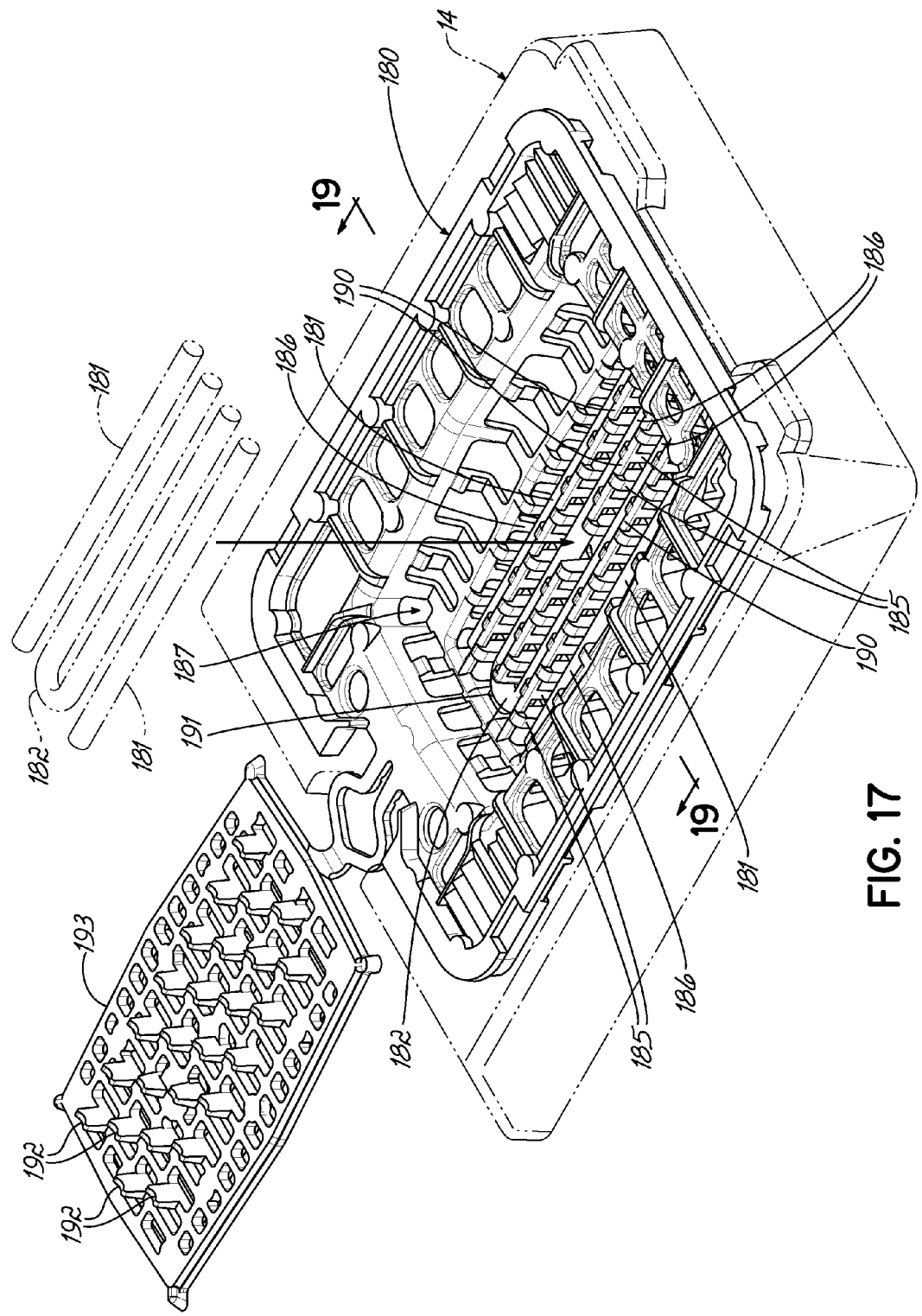
FIG. 17 is a perspective view of another embodiment of a tissue cassette and frame assembly showing tissue samples being placed into respective tissue receiving channels in the cassette.
Figure 18:
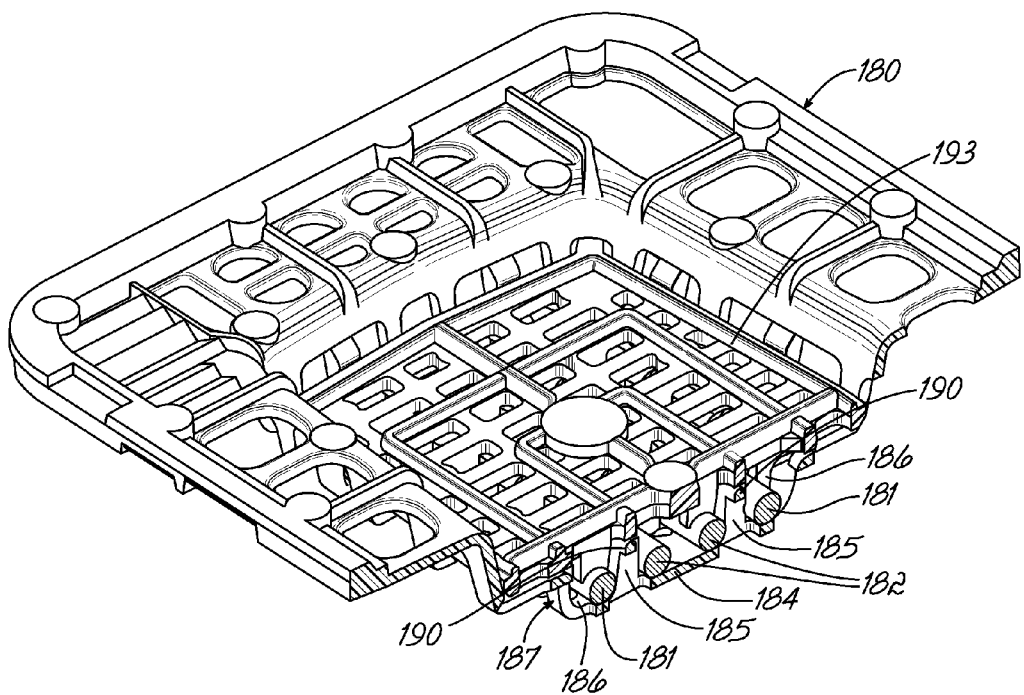
FIG. 18 is a cross sectional view taken generally along line 18-18 of FIG. 17.
Figure 19:
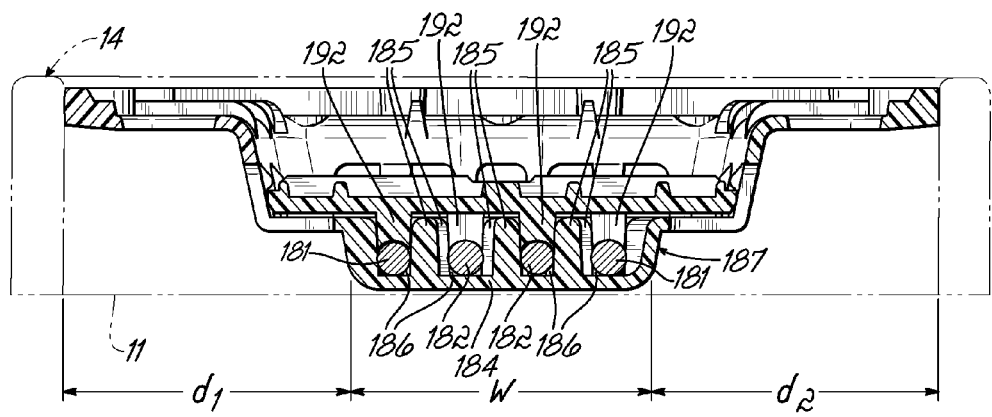
FIG. 19 is an end view, in cross section, of the cassette shown in FIGS. 17 and 18.

FIGS. 17-19 illustrate another embodiment of a microtome sectionable cassette 180 for holding elongated tissue samples 181, 182 in proper orientation throughout tissue processing, embedding and microtome sectioning. Note that tissue sample 182 is longer than samples 181 as will be discussed below. This embodiment is similar in many respects to the embodiment discussed in connection with FIG. 1. As best illustrated in FIGS. 18 and 19, the cassette 180 has a single continuous bottom wall 184 as opposed to the bottom wall sections 34 illustrated in connection with the first embodiment (FIG. 2). Respective tissue separating members 185 extend upwardly and are integrally formed with the bottom wall 184 and define tissue receiving channels or troughs 186 therebetween. The tissue containing portion 187 of the cassette has a width "w" which is less than the corresponding width of the tissue containing portion shown in FIG. 2. Thus, the distances $d_1$ and $d_2$ between the side of a mold (not shown) that will hold the cassette 180 and the side of the tissue containing portion 187 is greater in the embodiment of FIGS. 17-19. Therefore, anchoring of the cassette 180 within the paraffin 11 is more stable.

Respective support members or bars 190 are provided and connect the upstanding, staggered separating members 185 together. This is best shown in FIGS. 17 and 18. The bars 190 therefore provide deep anchoring elements in the paraffin. That is, as portions of the separating members 185 are thinly sliced by the microtome blade, after bottom wall 184 is "faced" off by the blade, the remaining portions of the members 185 are held firmly in the paraffin block by the bars 190 and do not "chip out" as the ribbons are cut. The members 185 are spaced apart along the channels 186 to allow infiltration of embedding material into engagement with the underside or undersurface of the bars 190. In addition, the central support structure has one or more spaces or interruptions 191 along its length for allowing an elongated tissue sample 182 to be wrapped around and extend into respective adjacent channels 186 as shown. In this embodiment, as opposed to having two sidewalls for each trough or channel as in the first embodiment, a single upstanding separating structure 185, 190 is disposed between adjacent troughs or channels 186. This embodiment further includes respective tabs 192 that register in alignment with each channel 186 with the tabs 192 being disposed on a lid 193, as shown, for bearing against and retaining the tissue samples 181, 182 against the bottom wall 184 of the cassette 180 as shown in FIG. 19. As with the other embodiments, resilient material, such as microtome sectionable foam (not shown), may be placed between the tabs 192 and the tissue samples 181, 182. This foam can account for or accommodate irregularly shaped samples, or variations in sample size to ensure that each tissue sample 181, 182 is firmly stabilized against the bottom 184 of the cassette 180.

The foam may be a flat flexible sheet of foam, or any other suitable shape, such as a ribbed sheet of foam in which the ribs of the foam align with the channels or troughs 186 in the cassette 180.

Figure 20:
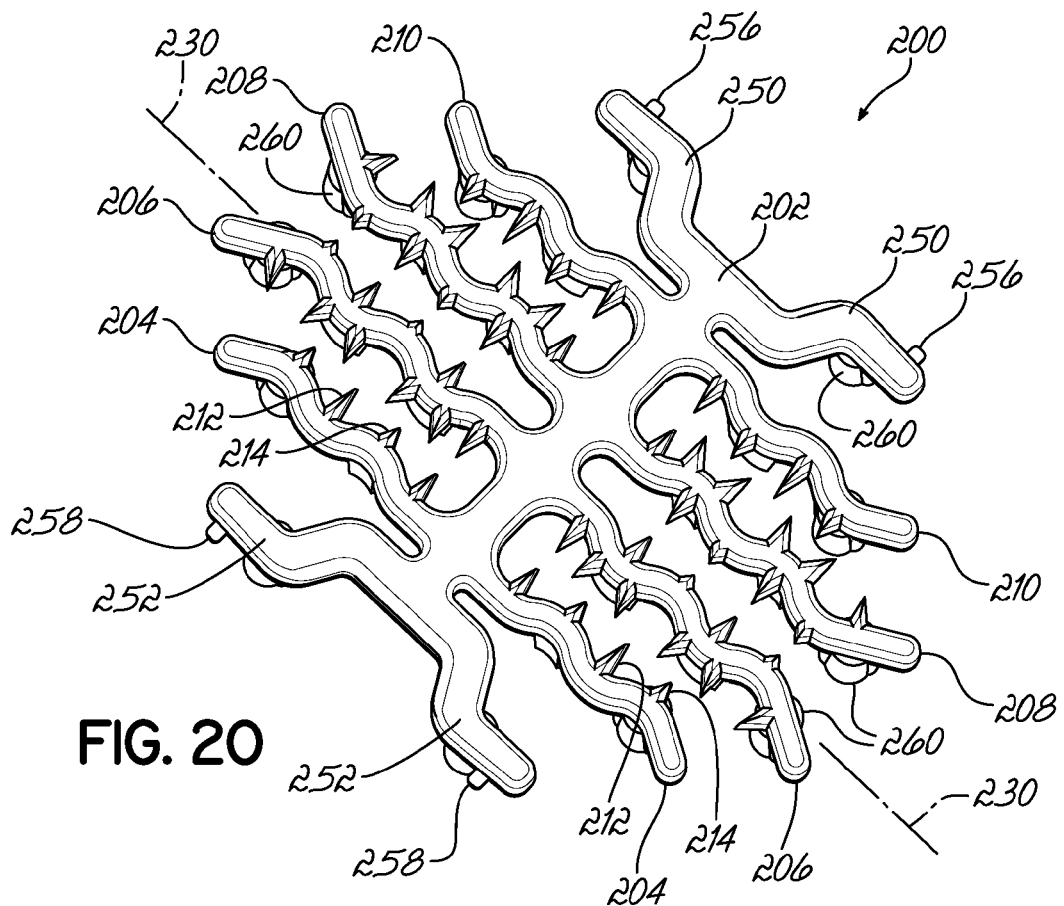
FIG. 20 is a perspective view of a tissue orientation device according to one embodiment and adapted to snap fit into a microtome sectionable cassette.
Figure 20A:
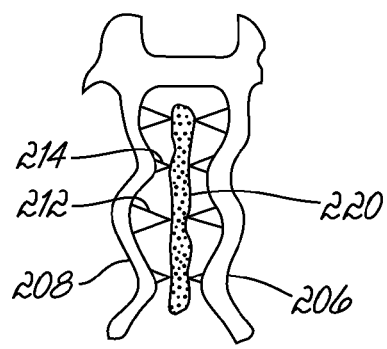
FIG. 20A is a top view of a portion of the tissue orientation device shown in FIG. 20.

A microtome sectionable tissue orientation device 200 is shown in FIGS. 20 and 20A. Preferably, the entire device is formed from a material that may be successfully sectioned in a microtome. The chosen material may be as described above in connection with the manufacture of cassette 12. The first embodiment includes a central spine 202 with symmetrically protruding legs 204, 206, 208, 210. Tissue engaging teeth 212 and 214 comprise sectionable, tissue contacting surfaces along each leg 204, 206, 208, 210. Note that teeth 214 are shorter than teeth 212, and this serves to center the tissue 220 in the passageway as shown in FIG. 20A. Long and short teeth 212, 214 alternate along each leg 204, 206, 208, 210 to correspond with undulations along the length of each leg. The teeth 212, 214 are alternated to provide a reasonably consistent overall distance between teeth 212, 214 on different legs 204, 206, 208, 210 despite the wavy or undulating nature of the leg 204, 206, 208, 210.

Each holding leg 204, 206, 208, 210 undulates along an axis 230 and the undulation shape is generally sinusoidal. This is to allow paraffin infiltration intimately against the tissue sample. The wavy or undulating design of the holding legs 204, 206, 208, 210 also helps prevent air bubbles from becoming trapped against or between the supporting legs and the tissue. Air bubbles can interfere with the quality of the microtome sectioning and resulting ribbons.

Figure 20B:
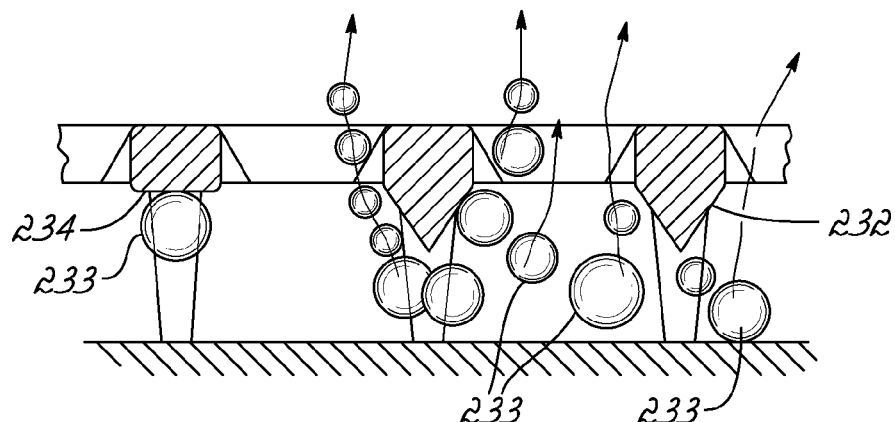
FIG. 20B is a schematic, cross sectional view of an alternative design for the tissue holding legs of FIGS. 20 and 20A.

As shown in FIG. 20B, the base of each holding leg can include a taper 232 to deflect bubbles 233 and to prevent them from being trapped under what would otherwise be a flat surface as shown at 234 in FIG. 20B.

Figure 20C:
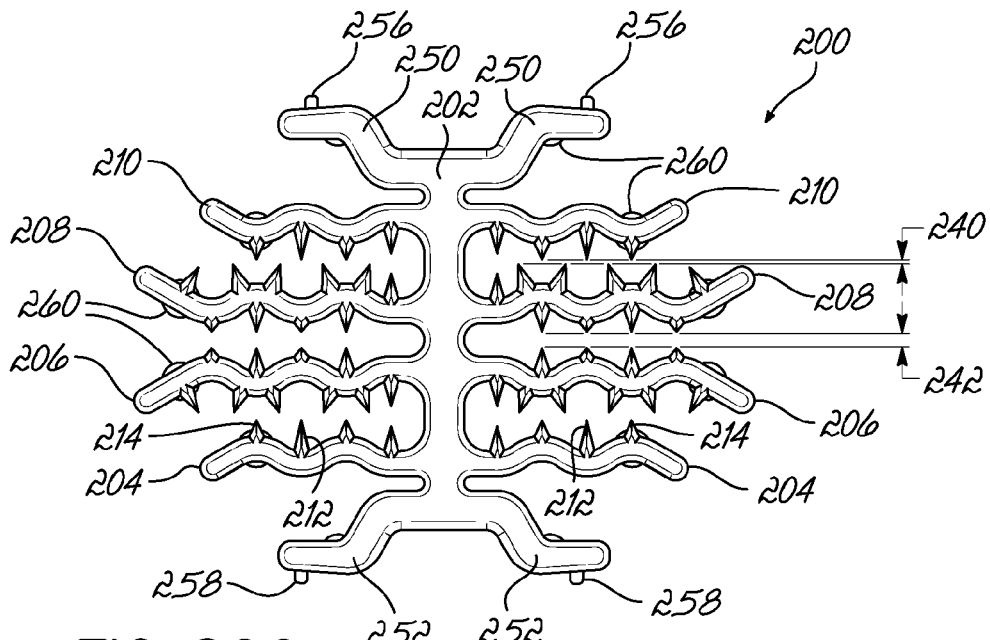
FIG. 20C is a top view of the tissue orientation device shown in FIG. 20.

The distance between each leg 204, 206, 208, 210 is designed to hold a specific range of tissue thicknesses. As shown in FIG. 20C, the distance between legs 208 and 210 represents a smaller space 240 than the space 242 between legs 206 and 208. This is to accommodate thicker tissues between legs 206 and 208 and thinner tissues between legs 208 and 210.

Figure 20D:
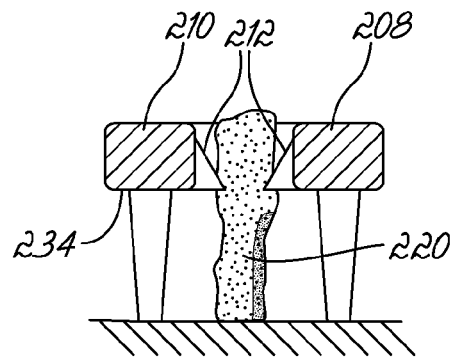
FIG. 20D is an enlarged cross sectional view of two tissue holding legs holding a tissue sample therebetween.

The teeth 212, 214 are tapered from the top down to make them one-directional as shown in FIG. 20D. This insures that the tissue 220 will insert easily and be less likely to back out.

In FIG. 20 further design details show legs 250, 252 which are somewhat flexible to allow for a small amount of preload and spring back or resilience when installing the orientation device 200 between the side walls of a sectionable cassette, such as a cassette as disclosed in one of the above-incorporated patents or applications, or as shown and described hereinbelow. Tabs 256, 258 lock the tissue orientation device 200 into the cassette walls by protruding through the openings in the cassette walls. This insures that the tissue orientation device 200 does not move within the cassette during tissue processing and embedding and maintains the desired orientation of the tissue samples 220 throughout any processing embedding and sectioning procedures.

Figure 21:
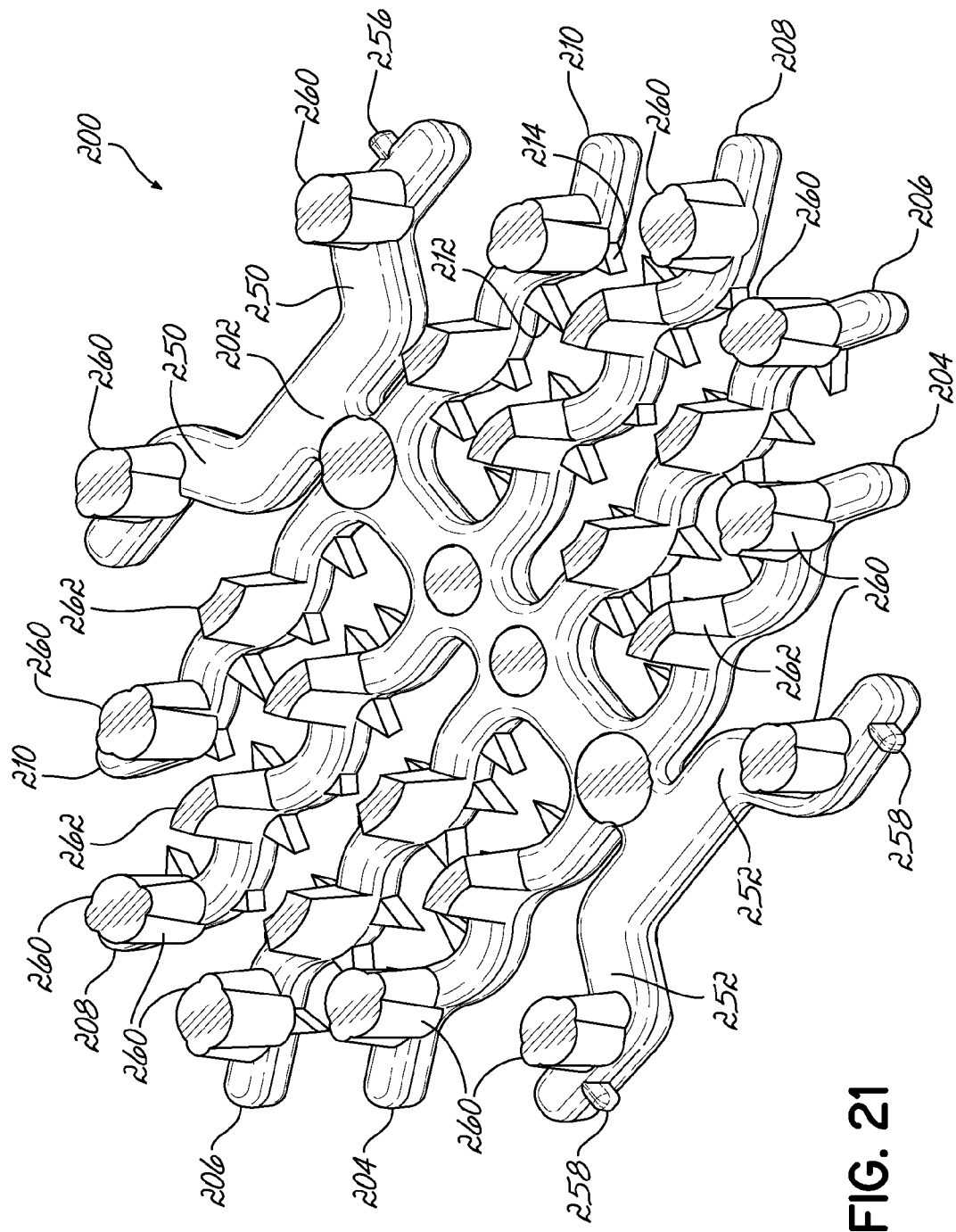
FIG. 21 is a bottom perspective view of the tissue orientation device of FIG. 20.

FIG. 21 shows a bottom perspective view of the orientation device 200 shown in FIG. 20. Standoff feet 260 and 262 on the bottom surface of the holding legs 204, 206, 208, 210 keep the orientation device 200 spaced away from the bottom plane of the cassette well (not shown). This allows full paraffin infiltration between the cassette well or interior bottom and the holding legs 204, 206, 208, 210 of the orientation device 200. Full paraffin infiltration will ensure that during the sectioning of the paraffin block using the microtome that only the standoff feet 260, 262 and the tissue 220 are exposed to the microtome blade. While the orientation device 200 is made of a sectionable material, high quality sections may be difficult to obtain when cutting through the entire orientation device 200. It is therefore optimal to have the holding legs 204, 206, 208, 210 spaced from the sectioning plane. This is also why the tissue 220 is placed between the legs 204, 206, 208, 210 and located at the bottom of the cassette well (not shown) which abuts the bottom of the standoff feet 260, 262. There are two different types of standoff feet shown - feet that are more trapezoidal in shape (262) and feet that are more cylindrical (260). The cylindrically shaped feet 260 are for ease of manufacturing since round pins are used to eject the plastic parts from the injection mold. Standoff feet of other configurations are acceptable as long as they allow for the paraffin to infiltrate around the tissue, do not trap bubbles, and are not sufficiently large so as to impede high quality microtome sectioning of the tissue contained therein and embedded in a hardened block of embedding material.

Figure 22:
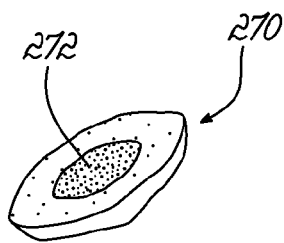
FIG. 22 is a perspective view of a skin tissue sample.
Figure 23:
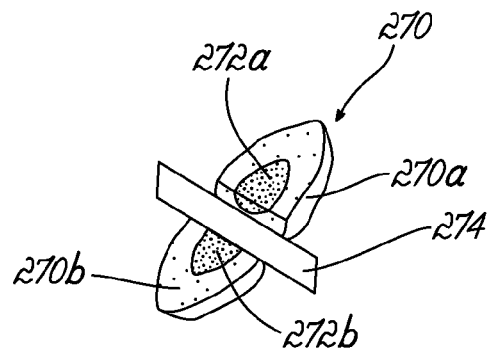
FIG. 23 is a perspective view of the skin tissue sample of FIG. 22 being transected into halves.
Figure 24:
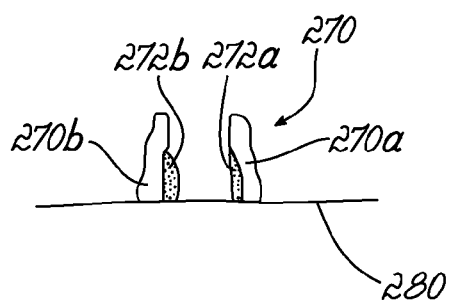
FIG. 24 is an elevational view of the two transected tissue sample halves oriented on a cutting plane.
Figure 25:
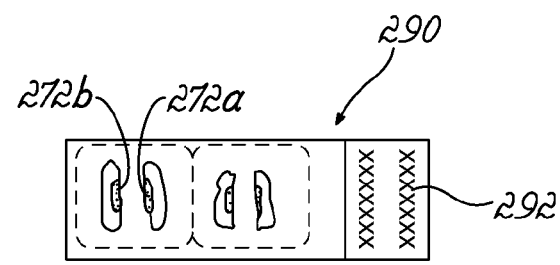
FIG. 25 is a top view of a microscope slide prepared with the tissue sample halves shown in FIG. 24, after microtome sectioning.

By way of example, FIG. 22 shows a shave biopsy 270 with a skin lesion 272. FIG. 23 depicts the transection of the biopsy 270 into halves 270a, 270b and lesion 272 into two parts 272a, 272b using a blade 274. FIG. 24 shows a side view depicting the proper orientation of the skin biopsies 270a, 270b in relationship to the microtome sectioning plane 280. As shown in FIG. 25, once embedded, sliced and placed on a glass slide 290, the stained sections will be examined by the pathologist. Note the orientation between the tissue samples 270a, 270b and the section plane 280 has been maintained throughout the entire process. An ID number 292 may be used to identify the slide 290 and tissue samples 270a, 270b.

Figure 26:
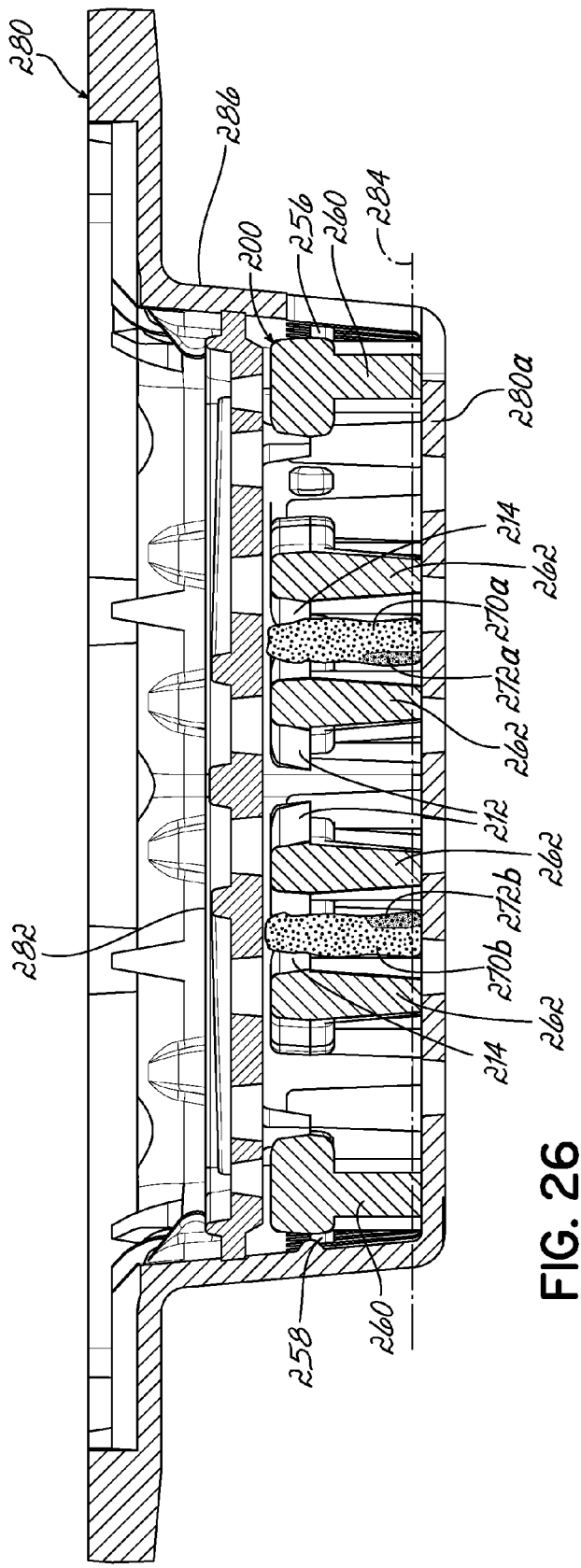
FIG. 26 is a cross sectional view of a microtome sectionable cassette holding the tissue orientation device and tissue samples therein.

FIG. 26, which is a cross-section through a sectionable tissue processing cassette 280 holding an orientation device 200, shows the orientation of the skin lesion biopsies 270a, 270b. Samples 270a, 270b are being held upright and perpendicular to the sectioning plane 280 as was shown in FIG. 5. As further shown, the tissue orientation device 200 is snap fit into the cassette 280 and retained or locked in place by tabs 256, 258 located on opposite sides of the device 200. As previously mentioned, these tabs 256, 258 can lock into suitable structure of the cassette, such as openings in the cassette 280. The cassette includes a lid 282 similar to the cassettes previously described. The lid 282 may be snapped downward into a locked position against the upper side of the tissue orientation device 200 to ensure that the feet 262 of the orientation device 200, as well as the tissue samples 270a, 270b are held against the bottom wall 280a of the cassette 280 in the sectioning plane 284. In this manner, it will be understood that sections may be taken by a microtome parallel with the section plane 284 after the cassette containment portion 286, assembled with the orientation device 200 and tissue samples 270a, 270b has been embedded in a block of material such as paraffin as described in the above incorporated patent and patent applications.

Many different configurations of the orientation device have been envisioned which solve orientation issues for different types of tissue. While the orientation device shown in FIGS. 20 and 21 is directed towards very thin, elongated skin biopsies, it would not be useful when the biopsies become too thick to be comfortably placed between the holding legs. Wider spaces and different alignment configurations are disclosed for larger tissue samples.

Figure 27:
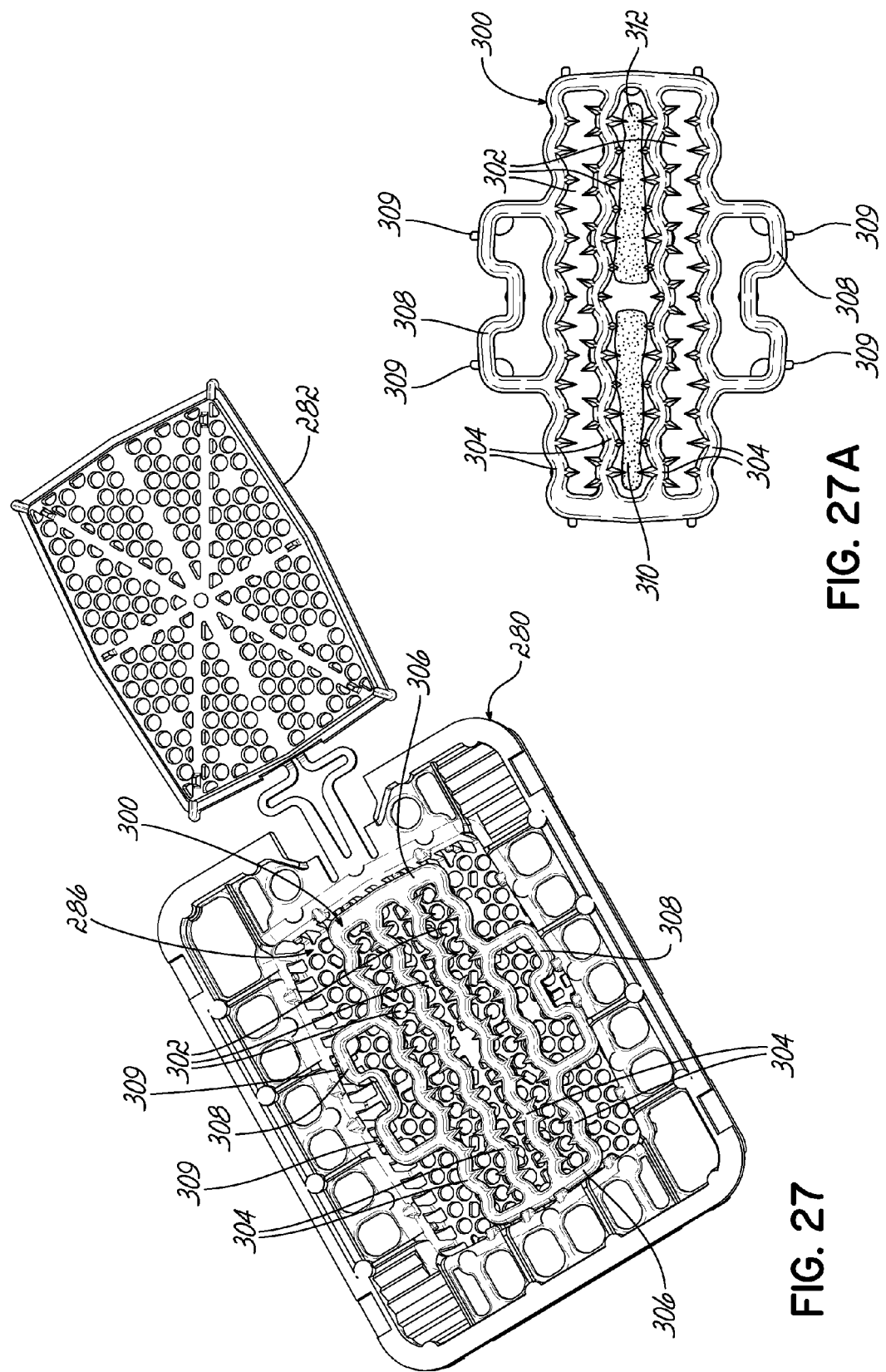
FIG. 27 is a top perspective view of a microtome sectionable cassette holding a tissue orientation device constructed in accordance with another embodiment.

FIG. 27 shows a tissue orientation device 300 constructed with most of the same features as those shown in FIGS. 20 and 21 and retained in a microtome sectionable cassette 280. There are three elongated central passageways 302 which can accept tissue. These passageways 302 are formed by long, generally parallel holding legs 304. The legs 304 are connected to each other by side walls 306 rather than the central spine of FIG. 20. Again, each holding leg 304 has a serpentine or undulating configuration with tissue engaging teeth to insure the tissue is held securely and does not move during processing. This design allows the technician to use the central area for tissues which may be thicker than those used in the orientation device 200 shown in FIG. 20. Because these holding legs 304 are so long it is possible to deflect them more at the center than at the ends. Some tissue samples are wedge-shaped. The thicker portion of the wedge can be placed at the center sections of the holding legs 304. The thinner portion of the wedge will be held tightly towards the periphery of the passageway 302 where the legs 304 are attached to the side walls 306. Outer locking legs 308 with locking elements 309 hold the device 300 in the containment portion 286 of the cassette 280. FIG. 27A shows a top view of the orientation device 300 with wedge shaped tissues 310 and 312 installed in the central area of the tissue orientation device shown in FIG. 27.

Figure 28:
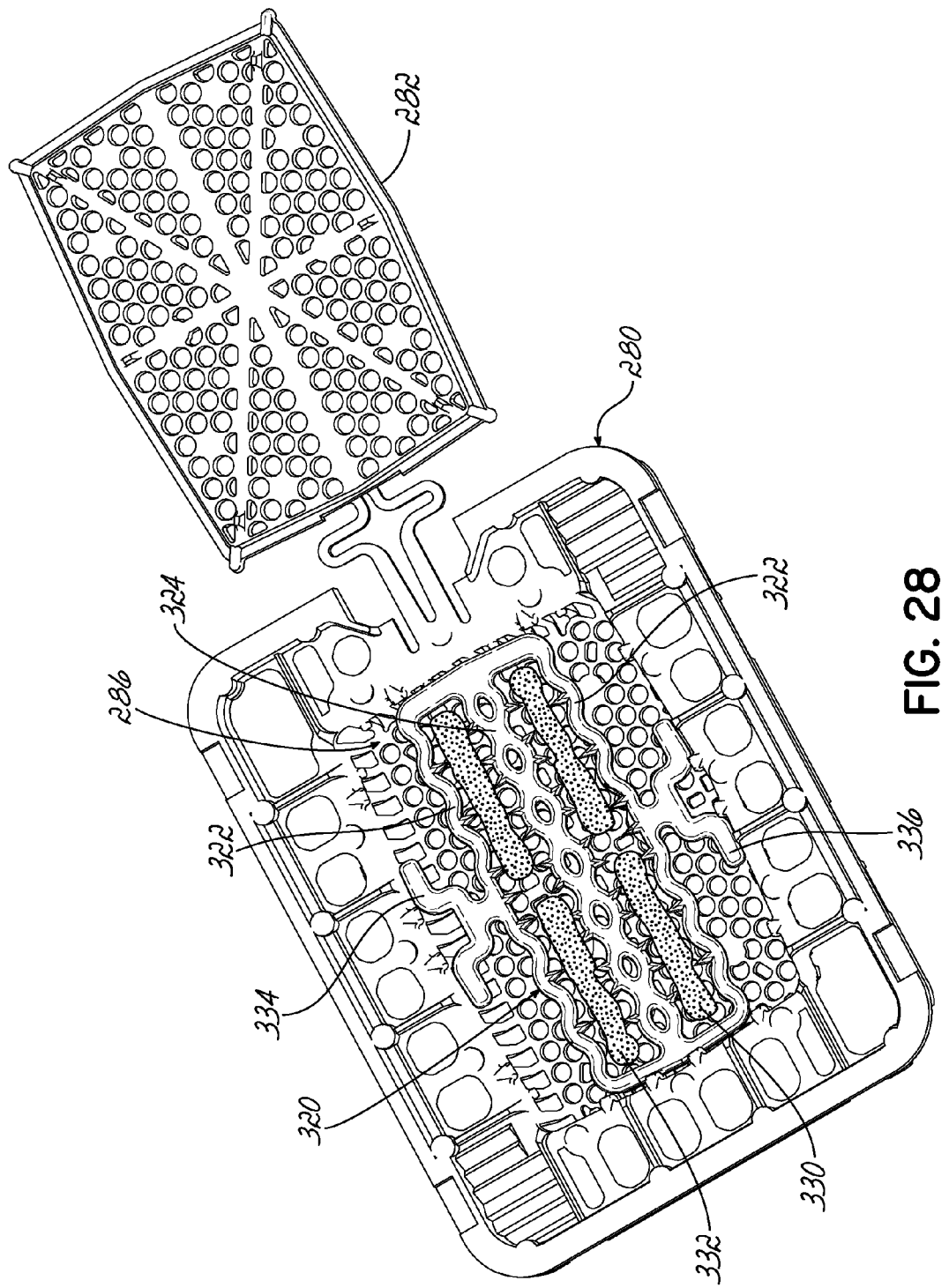
FIG. 28 is a top perspective view of a microtome sectionable cassette holding a tissue orientation device constructed in accordance with another embodiment.

FIG. 28 shows another embodiment of the tissue orientation device 320 whereby two elongated spaces respectively between outer legs 322 and a central leg 324 are provided for tissue alignment. Tissue items 330 and 332 as shown here represent gallbladder tissue which must be oriented on edge. Elongated biopsies such as those produced from needle biopsy tools could also be used in an alignment device 320 depicted in FIG. 28. This design has somewhat more rigid holding legs 322, 324 than in the devices of FIGS. 20 and 27 and more narrow passageways to accommodate the long and narrow tissue samples 330, 332. The device 320 includes resilient legs 334, 336 to clip into the well or containment space of a sectionable cassette 340 having a hinged lid 342 as, for example, disclosed in the above-incorporated patents and/or patent applications.

Figure 29:
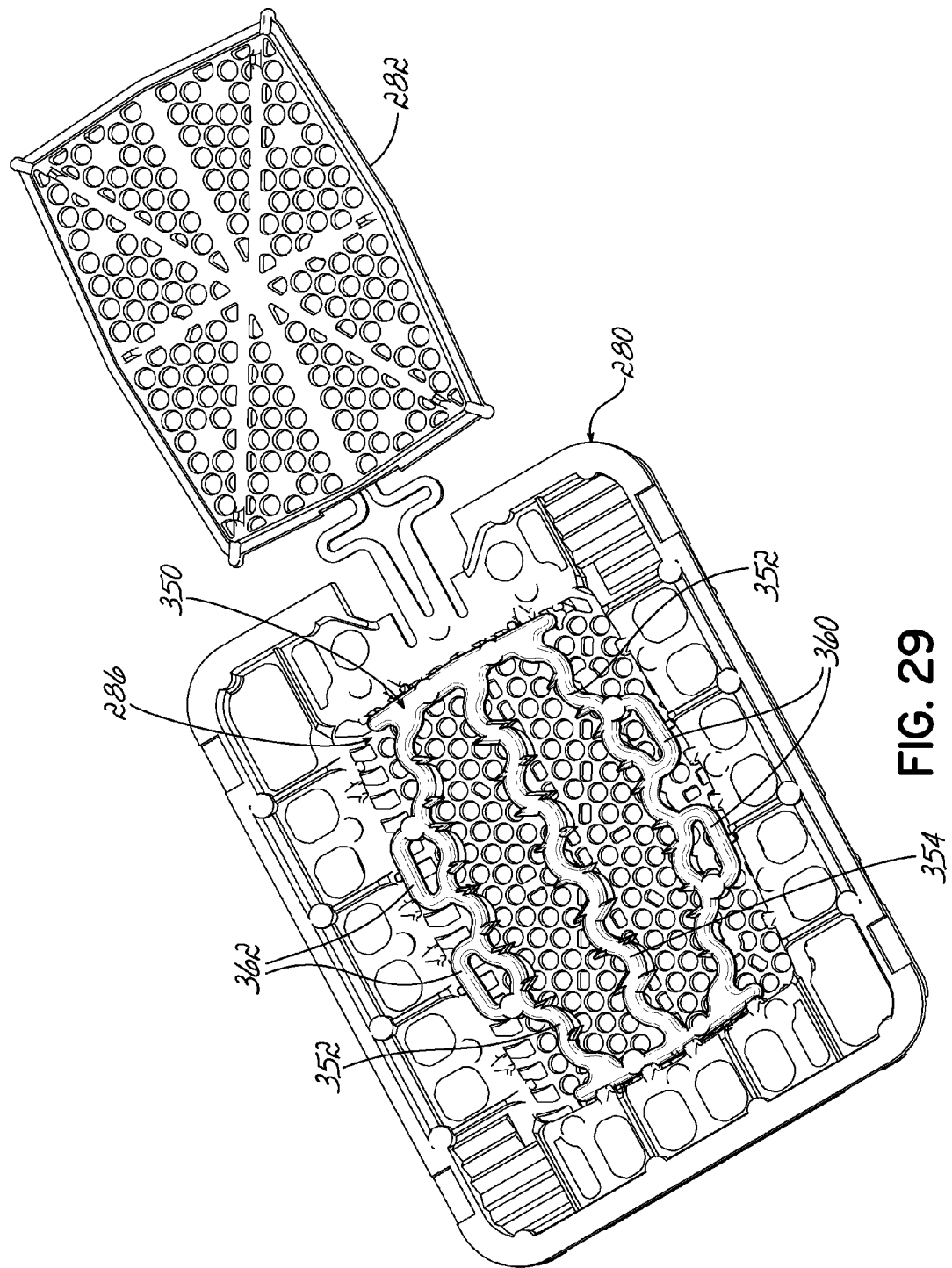
FIG. 29 is a top perspective view of a microtome sectionable cassette holding a tissue orientation device constructed in accordance with another embodiment.

FIG. 29 shows another tissue orientation device 350 with even larger passageways between the holding legs 352, 354. These tissue passageways could be used where it is desirable for the tissue to be segregated into separate halves. This is often done for reasons of staging disease in specific areas of a small organ. For instance, if the prostate is removed, the left half might be segregated from the right half to make sure that the pathologist can differentiate the margins of clear tissue between the two halves. As with the previous embodiments, locking legs 360, 362 are provided for snap fitting or friction fitting the device 350 in the containment portion or well 286 of the cassette 280.

By way of summary, the undulating, wavy or serpentine legs of the orientation devices allow tissue to be gently held in an oriented fashion, but also allow the clearance of air bubbles during the embedding process and the infiltration of processing chemicals and paraffin. The peripheral features of the orientation devices, such as the resilient outer legs, engage the sectionable cassette to prevent dislodgement of the orientation device and tissue samples during processing and embedding. Other features establish minimum distance between the tissue and the sidewalls of the cassette for proper sectioning and microscope slide layouts. The standoff feet of the orientation devices are positioned to support the tissue along the holding legs so that the tissue cannot migrate beneath the legs and become dislodged or malpositioned. The elongated tissue holding legs are flexible yet provide support to hold proper orientation of the tissue during processing and embedding. Flexibility of the holding legs helps to install the tissue in the orientation device. Tissue engaging teeth on the holding legs can have a one way configuration that allows the tissue to be inserted in one direction but resists any backing out of the tissue during insertion stages and also during the hydraulic tissue processing steps. The teeth also helps to space the tissue away from the legs to allow for complete infiltration of processing fluids and paraffin.

While the present invention has been illustrated by a description of various illustrative embodiments and while these embodiments have been described in some detail, it is not the intention of the Applicants to restrict or in any way limit the scope of the appended claims to such detail. Additional advantages and modifications will readily appear to those skilled in the art. The various features disclosed herein may be used alone or any combinations depending on the needs and preferences of the user. However, the invention itself should only be defined by the appended claims. What is claimed is:

What is claimed is:

1. A method for preparing one or more elongated biopsy tissue samples for histological examination, comprising:
    positioning an elongated tissue sample in a first elongated channel of a perforated microtome sectionable support, the microtome sectionable support including a tissue cassette having a perforated bottom wall and at least one perforated side wall for defining a tissue sample receiving space;
    extending the elongated tissue sample from the first elongated channel to a second elongated channel segregated from the first elongated channel by separating structure;
    using biasing structure that extends into the first and second channels to hold the tissue sample against the bottom wall;
    subjecting the microtome sectionable support and the tissue sample to a process that replaces fluid in the tissue sample with a hardenable material;
    embedding the microtome sectionable support and the tissue sample in an embedding material;
    hardening the embedding material into a block; and
    slicing the block with a microtome into thin slices of the embedding material, the microtome sectionable support and the tissue sample.

2. The method of claim 1, further comprising:
    holding the tissue sample in a desired orientation using resilient fingers on opposite sides of the channel.

3. The method of claim 1, wherein the microtome sectionable support further comprises a resilient cellular material, and holding the tissue sample against the bottom surface further comprises:
    positioning the resilient cellular material between a lid and the tissue sample to trap the tissue sample between the resilient cellular material and the bottom surface.

4. The method of claim 3, wherein the resilient cellular material deforms during the immobilizing step to create a three dimensional space that receives the tissue sample.

5. The method of claim 1, wherein the microtome sectionable support is coupled to a frame prior to being subjected to the process for replacing fluid in the tissue sample with the hardenable material, and the method further comprises securing the frame in the microtome prior to slicing the block.

6. The method of claim 5, wherein prior to embedding the microtome sectionable support, resilient cellular material and the tissue sample in the embedding material, the microtome sectionable support is moved from a first position within the frame to a second position in which the support, resilient cellular material and tissue sample are exposed for simultaneous sectioning in the microtome.

7. A method for preparing one or more elongated biopsy tissue samples for histological examination, comprising:
    positioning a tissue sample in a first elongated channel of a perforated microtome sectionable support including a tissue cassette having a perforated bottom wall and at least one perforated side wall for defining a tissue sample receiving space;
    resiliently engaging the tissue sample with fingers positioned on opposite sides of the channel;
    using biasing structure that extends into the first channel to hold the tissue sample against the bottom wall;
    subjecting the microtome sectionable support and the tissue sample to a process that replaces fluid in the tissue sample with a hardenable material;
    embedding the microtome sectionable support and the tissue sample in an embedding material;
    hardening the embedding material into a block; and
    slicing the block with a microtome into thin slices of the embedding material, the microtome sectionable support and the tissue sample.

* * * * *